(12) United States Patent
Eriksson et al.

(10) Patent No.: US 7,528,156 B2
(45) Date of Patent: *May 5, 2009

(54) COMPOUNDS

(75) Inventors: Tomas Eriksson, Lund (SE); Tomas Klingstedt, Lund (SE); Tesfaledet Mussie, Lund (SE)

(73) Assignee: AstraZeneca AB (SE)

( * ) Notice: Subject to any disclaimer, the term of this patent is extended or adjusted under 35 U.S.C. 154(b) by 509 days.

This patent is subject to a terminal disclaimer.

(21) Appl. No.: 10/994,683

(22) Filed: Nov. 22, 2004

(65) Prior Publication Data

US 2005/0090494 A1  Apr. 28, 2005

Related U.S. Application Data

(63) Continuation of application No. 10/311,841, filed as application No. PCT/SE01/01377 on Jun. 14, 2001, now Pat. No. 6,911,458.

(30) Foreign Application Priority Data

Jun. 20, 2000 (SE) .................... 0002331
Dec. 5, 2000 (SE) .................... 0004480

(51) Int. Cl.
*A61K 31/445* (2006.01)
*C07D 211/58* (2006.01)

(52) U.S. Cl. ............ 514/329; 514/381; 514/397; 514/409; 514/422; 514/428; 546/223; 548/250; 548/314.7; 548/364.1; 548/517; 548/518; 548/569

(58) Field of Classification Search ........... 514/381, 514/397, 406, 422, 428, 329; 546/376.4, 546/223; 548/250, 314.7, 364.1, 517, 518, 548/567

See application file for complete search history.

(56) References Cited

U.S. PATENT DOCUMENTS

| | | | |
|---|---|---|---|
| 3,203,992 A | 8/1965 | Kunz et al. | |
| 3,577,432 A | 5/1971 | Helsley | |
| 3,755,584 A | 8/1973 | Plotnikoff et al. | |
| 3,818,017 A | 6/1974 | Janssen et al. | |
| 3,894,030 A | 7/1975 | Janssen et al. | |
| 3,929,768 A | 12/1975 | Brattsand et al. | |
| 3,994,974 A | 11/1976 | Murakami et al. | |
| 4,029,801 A | 6/1977 | Cavalla et al. | |
| 4,080,328 A | 3/1978 | Maruyama et al. | |
| 4,166,119 A | 8/1979 | Effland et al. | |
| 4,264,613 A | 4/1981 | Regnier et al. | |
| 4,304,915 A | 12/1981 | Berthold | |
| 4,338,323 A | 7/1982 | Regnier et al. | |
| 4,579,854 A | 4/1986 | Iwakuma et al. | |
| 5,576,321 A | 11/1996 | Krushinski, Jr. et al. | |
| 5,614,523 A | 3/1997 | Audia et al. | |
| 5,614,533 A | 3/1997 | Anderson et al. | |
| 5,627,196 A | 5/1997 | Audia et al. | |
| 5,741,789 A | 4/1998 | Hibschman et al. | |
| 5,789,402 A | 8/1998 | Audia et al. | |
| 6,518,286 B1 | 2/2003 | Baxter et al. | |
| 6,911,458 B2 * | 6/2005 | Eriksson et al. | 514/329 |
| 6,927,222 B2 * | 8/2005 | Hansen et al. | 514/292 |
| 6,943,188 B2 * | 9/2005 | Eriksson et al. | 514/424 |
| 6,951,874 B2 * | 10/2005 | Hansen et al. | 514/323 |
| 7,005,439 B2 | 2/2006 | Eriksson et al. | |
| 7,345,063 B2 | 3/2008 | Eriksson et al. | |
| 7,388,020 B2 | 6/2008 | Eriksson et al. | |
| 2003/0055080 A1 | 3/2003 | Forner et al. | |
| 2005/0090494 A1 | 4/2005 | Eriksson et al. | |
| 2005/0239801 A1 | 10/2005 | Eriksson et al. | |
| 2008/0176902 A1 | 7/2008 | Giovannini et al. | |
| 2008/0194632 A1 | 8/2008 | Giovannini et al. | |
| 2008/0227817 A1 | 9/2008 | Giovannini et al. | |

FOREIGN PATENT DOCUMENTS

| | | |
|---|---|---|
| DE | 2323215 | 11/1973 |
| DE | 37 23 568 | 1/1989 |
| DE | 37 23 648 | 1/1989 |
| DE | 4129535 | 3/1992 |
| DE | 197 03 131 A1 | 7/1998 |
| DE | 197 55 268 | 6/1999 |
| EP | 0 095 454 A2 | 11/1983 |
| EP | 0 128 007 A2 | 12/1984 |
| EP | 0 496 691 A1 | 7/1992 |
| EP | 0 587 311 A1 | 3/1994 |
| EP | 0 722 941 A2 | 7/1996 |
| EP | 0 903 349 A2 | 3/1999 |
| EP | 1389616 | 2/2004 |
| EP | 1263724 | 5/2005 |

(Continued)

OTHER PUBLICATIONS

Rollins chemokines Blood, vo. 90 (3) p. 909-928 (1997).*

(Continued)

*Primary Examiner*—Celia Chang
(74) *Attorney, Agent, or Firm*—Fish & Richardson P.C.

(57) ABSTRACT

The invention provides compounds of general formula (I) wherein m, n, Q, Z1, Z2, R1, R2, R3, R4, R5, R6, R7, and R8 are as defined in the specification, processes for their preparation, pharmaceutical compositions containing them and their use in therapy.

(I)

23 Claims, No Drawings

FOREIGN PATENT DOCUMENTS

| | | |
|---|---|---|
| FR | 2.190.430 | 6/1972 |
| GB | 1368012 | 9/1974 |
| GB | 2373186 | 9/2002 |
| WO | WO 92/05147 | 4/1992 |
| WO | WO 93/25528 | 12/1993 |
| WO | WO 97/22596 | 6/1997 |
| WO | WO 97/23458 | 7/1997 |
| WO | WO 97/30035 | 8/1997 |
| WO | WO 97/32856 | 9/1997 |
| WO | WO 98/13354 | 4/1998 |
| WO | WO 98/32442 | 7/1998 |
| WO | WO 99/02166 | 1/1999 |
| WO | WO 99/25686 | 5/1999 |
| WO | WO 99/31092 | 6/1999 |
| WO | WO 99/65895 | 12/1999 |
| WO | WO 00/31033 | 6/2000 |
| WO | WO 00/35449 | 6/2000 |
| WO | WO 00/35451 | 6/2000 |
| WO | WO 00/40529 | 7/2000 |
| WO | WO 00/41669 | 7/2000 |
| WO | WO 00/53187 | 9/2000 |
| WO | WO 00/53600 | 9/2000 |
| WO | WO 00/58305 | 10/2000 |
| WO | WO 00/69820 | 11/2000 |
| WO | WO 00/75114 | 12/2000 |
| WO | WO 01/14333 A1 | 3/2001 |
| WO | WO 01/43744 | 6/2001 |
| WO | WO 01/44227 | 6/2001 |
| WO | WO 01/06279 | 8/2001 |
| WO | WO 01/62728 | 8/2001 |
| WO | WO 01/62757 | 8/2001 |
| WO | WO 01/87839 A1 | 11/2001 |
| WO | WO 01/89492 | 11/2001 |
| WO | WO 01/92224 | 12/2001 |
| WO | WO 01/98270 | 12/2001 |
| WO | WO 01/98272 | 12/2001 |
| WO | WO 01/98273 | 12/2001 |
| WO | WO 02/04434 | 1/2002 |
| WO | WO 02/08213 | 1/2002 |
| WO | WO 2002/00679 | 1/2002 |
| WO | WO 02/12265 | 2/2002 |
| WO | WO 02/12266 | 2/2002 |
| WO | WO 02/20484 | 3/2002 |
| WO | WO 02/45703 | 6/2002 |
| WO | WO 02/076933 | 10/2002 |
| WO | WO 02/076948 | 10/2002 |
| WO | WO 02/079156 | 10/2002 |
| WO | WO 02/088167 | 11/2002 |
| WO | WO 03/042178 | 5/2003 |
| WO | WO 2003/042164 | 5/2003 |
| WO | WO 03/051839 | 6/2003 |
| WO | WO 03/068743 | 8/2003 |
| WO | WO 03/080574 | 10/2003 |
| WO | WO 03/082292 | 10/2003 |
| WO | WO 2004/032921 | 4/2004 |
| WO | WO 2005/010154 | 2/2005 |
| WO | WO 2005/025555 | 3/2005 |
| WO | WO 2005/041980 | 5/2005 |
| WO | WO 2007/015664 | 2/2007 |
| WO | WO 2007/015666 | 2/2007 |
| WO | WO 2007/015667 | 2/2007 |
| WO | WO 2007/015668 | 2/2007 |
| WO | WO 2007/024182 | 3/2007 |
| WO | WO 2007/024183 | 3/2007 |
| WO | WO 2007/053082 | 5/2007 |

OTHER PUBLICATIONS

Cohen et al. "Cytokine funstion . . . " CA 125:31527 (1996).*
Hansen et al. "prepartion of substituted . . . " CA 135:195501 (2001).*
Eriksson et al. "Preparation of . . . " Ca 136:69740 (2001).*
Mirzadegan et al. "Identification of the binding site for . . . " J. Biol. chem. v. 275, p. 25562-25571 (2000).*
Zhou et al. "alph-aminothiazole- . . . " Bioorg. Med. Chem. Lett. vo. 17, p. 309-314 (2007).*
Saeki et al. "CCR1 chemokine receptor . . . " Current pharmc. design v. 9, p. 1201-12-8 (2003).*
U.S. Appl. No. 10/204,754, filed Aug. 23, 2002, Hansen et al.
U.S. Appl. No. 10/204,789, filed Aug. 23, 2002, Hansen et al.
U.S. Appl. No. 10/204,790, filed Aug. 23, 2002, Bodkin et al.
U.S. Appl. No. 10/311,667, filed Dec. 17, 2002, Eriksson et al.
U.S. Appl. No. 10/468,179, filed Sep. 11, 2003, Brough et al.
U.S. Appl. No. 10/472,017, filed Sep. 19, 2003, Eriksson et al.
U.S. Appl. No. 10/472,412, filed Sep. 19, 2003, Eriksson et al.
Archibald et al., "Antiinflammatory 4-acylaminopiperidines", *CAPLUS* 77:34355 (1972).
Cattanach, Christopher J. et al., "Studies in the Indole Series. Part IV. Tetrahydro-5H-pyrido[4, 3-b]indoles as serotonin antagonists," J. Chem. Soc. C., vol. 10, p. 1235-1243 (1968).
Cohen et al., "Cytokine function: A study in biologic diversity", *CAPLUS* 125:31527 (1996).
Friebe et al., "Piperidinopropyl derivatives and pharmaceutical compositions containing them", *CAPLUS* 94:103172 (1981).
Hesselgesser, Joseph et al., "Identification and Characterization of Small Molecule Functional Antagonists of the CCR1 Chemokine Receptor," The Journal of Biological Chemistry, vol. 273, No. 25, pp. 15687-15692 (1998).
Howard, O.M. Zack, et al., "Chemokines: progress toward identifying molecular targets for therapeutic agents," Trends in Biotechnology, vol. 14, pp. 46-51 (1996).
Janda, Manabu Hori Kim D., "A Soluable Polymer Approach to the "Fishing Out" Principle: Synthesis and Purification of β-Amino Alcohols," J. Org. Chem, vol. 63, pp. 889-894 (1998).
Komai, Tomoaki, et al. "Structure-Activity Relationships of HIV-1 PR Inhibitors Containg AHPBA-II. Modification of Pyrrolidine Ring at P1' Proline," Bioorganic & Medicinal Chemistry, vol. 4, No. 8, pp. 1365-1933 (1996).
Leclerc et al., "Derivatives Related to Betaxolol with α-and β-Adrenergic Activities", *Arzneim.-Forsch/Drug. Res.* 35(11):1357-1367 (1985).
Meurer et al., "Discovery of potent human CCR5 antagonists for the treatment of HIV-1 infection—II.", *CAPLUS* 2000:331722 (2000).
Navas, III, Frank et al., "The Design and Synthesis of a Hapten for 1192U90, A Potential Atypical Antipsychotic Agent," Synthetic Communications, vol. 26, No. 7, pp. 1411-1421 (1996).
Payard, Marc et al., "N-Aminomethylated Derivatives of Some Hydroxamic Acids as Anti-Inflammatories," Eur. J. Med. Chem., pp. 1-10 (Jan. 21, 1975).
Rubini et al., "Synthesis of Isosteric Methylene-Oxy Pseudodipeptide Analogues as Novel Amide Bond Surrogate Units", *Tetrahedron* 42(21):6039-6045 (1986).
STN International, File CAPLUS, CAPLUS Accession No. 1968. 402884.
Timmermans et al., "Hypotensive Properties of Benzodioxane Derivatives Structurally Related to R 28935. Comparison of Activity with some Receptor Affinities", *Arch. int. Pharmacodyn.* 255:321-334 (1982).
Wright, Jon L. et al., "Discovery of Selective Dopamine D4 Receptor Antagonists: 1-Aryloxy-3-(4-Aryloxypiperidinyl)-2-Propanols", vol. 7, No. 11, Bioorganic & Medicinal Chemistry Letters, 1377-1380 (1997).
Alcaraz et al., "Preparation of piperidinyl alcohols as chemokine receptor modulators for treatment of diseases such as asthma", *CAPLUS* 139:197375 (2003).
Barnes et al., "COPD: is there light at the end of the tunnel?", *Curr Opin Pharmacol* 4:263-272 (2004).
Barnes et al., "Prospects for new drugs for chronic obstructive pulmonary", *Lancet* 364:985-996 (2004).
Bechtloff et al., "Pseudopolymorphs in industrial use", *SciSearch* 10289666 (2001).
Berthold, "3-Aminopropoxyaryl derivatives", *CAPLUS* 93:8015 (1980).
Black et al., "Increased chemical purity using a hydrate", *SciSearch* 12765805 (2004).

Chou et al., "Adrenergic regulation of macrophage-derived tumor necrosis factor-α generation during a chronic polyarthritis pain model", *CAPLUS* 129:3784 (1998).

de Boer, "Potential new drugs for therapy of chronic obstructive pulmonary disease", *Expert Opin. Investig. Drugs* 12:1067-1086 (2003).

Eriksson et al., "Preparation of benzimidazol derivatives as modulators of chemokine receptors", *CAPLUS* 137:247698 (2002).

Exhibit A CAS search result.

Hu et al., "Dependence of the chemical dynamics of intercluster association reactions on the strength of the solute-solvent intermolecular potential", *Beilstein Abs*. 5809171 (1993).

Katritsky et al., "Heterocyclic Chemistry", Cambridge, p. 75 (1964).

Levine, "β2-Andrenergic mechanisms in experimental arthritis", *CAPLUS* 109:52680 (1988).

Matsuo et al., "Preparation of N-pentadienoylaminoalkyl-4-(3-indolyl) piperidines and analogs as antiallergic agents", *CAPLUS* 115:232091 (1991).

Mizuhashi, "A guinea pig model of propranolol-induced bronchoconstriction (PIB) after allergic immediate asthmatic reaction and the role of thromboxane A2 and 5-lipoxygenase products", *CAPLUS* 122:71729 (1995).

Saeki, "Molecular mechanism of rheumatoid arthritis and relationship between cytokine and chronic rheumatoid arthritis", *CAPLUS* 125:272100 (1996).

Schmidt et al., "Molecular mechanisms in allergy and clinical immunology", *J Allergy Clin Immunol* 105:673-682 (2000).

Tanabe et al., "Propanol derivatives as antihypertensives", *CAPLUS* 96:110143 (1982).

Tanaka et al., "Antiallergic effects of a novel compound, SWR-00151", *CAPLUS* 126:311929 (1997).

Wright et al., "Subtype-Selective N-Methyl-D-Aspartate Receptor Antagonists: Synthesis and Biological Evaluation of 1-(Heteroarylalkynl)-4-benzylpiperidines", *CAPLUS* 133:321781 (2000).

Yamamoto, "Expression of monocyte chemotactic activity by crosslinked dimerization of a ribosomal protein", *CAPLUS* 127:64176 (1997).

Zenitz et al., "3-(Piperidino-lower-alkyl) indoles", *CAPLUS* 87:102164 (1977).

Braga et al., "Making crystals from crystals: a green route to crystal engineering and polymorphism", *Chem. Commun*. 3635-3645 (2005).

de Boer, "Potential new drugs for therpy of chronic obstructive pulmonary disease", *Expert Opin. Investig. Drugs* 12:1067-1086 (2003).

Edenhofer et al., "Hypotensive aromatic ethers and their pharmaceutical compositions", *CAPLUS* 73:87939 (1970).

Finlayson et al., "Acquired QT interval prolongation and HERG: implications for durg discovery and development", *Eur. J. Pharm*. 500:129-142 (2004).

Guillaumel et al., "Recherches sur les dérivés nitrés d'intérêt biologique", " *Eur. J. Med. Chem*. 18(5):431-436 (1983).

Haverkamp et al., "The potential for QT prolongation and proarrhythmia by non-antiarrhythmic drugs: clinical and regulatory implications", *Eur Heart J* 21:1216-1231 (2000).

Kirk-Othmer, "Crystallization" in: *Encyclopedia of Chemical Technology* (2002 ed.), pp. 95-147.

Kiss et al., "High Throughput Ion-Channel Pharmacology: Planar-Array-Based Voltage Clamp", *Assay Drug Dev. Technol*. 127-135 (2003).

Sanguinetti et al., "A Mechanistic Link between an Inherited and an Acquired Cardiac Arrhythmia: *HERG* Encodes the $I_{Kr}$ Potassium Channel", *Cell* 81:299-307 (1995).

Seddon, "Pseudopolymorph: A Polemic", Crystal Growth & Design 4(6):1087, 2 web pages (2004).

Thalén and Brattsand, "Synthesis and Anti-inflammatory Properties of Budesonide, A New Non-halogenated Glucocorticoid with High Local Activity", *Arzneim.-Forch./Drug Res*. 29(II):1687-1690 (1979).

Tomlinson et al., "Efficacy of low and high dose inhaled corticosteroid in smokers versus non-smokers with mild ashtma", *Thorax* 60:282-287 (2005).

\* cited by examiner

COMPOUNDS

CROSS-REFERENCE TO RELATED APPLICATIONS

This application is a continuation of U.S. application Ser. No. 10/311,841, filed on Feb. 19, 2003 (Now U.S. Pat. No. 6,911,458), which is the National Stage under 35 U.S.C. § 371 of International Application No. PCT/SE01/01377 which has an International filing date of Jun. 14, 2001, which designated the United States of America, and claims priority benefit of SE 000233-7, filed Jun. 20, 2000, and SE 0004480-0, filed Dec. 5, 2000.

The present invention relates to novel compounds, processes for their preparation, pharmaceutical compositions containing them and their use in therapy.

Chemokines play an important role in immune and inflammatory responses in various diseases and disorders, including asthma and allergic diseases, as well as autoimmmune pathologies such as rheumatoid arthritis and atherosclerosis. These small secreted molecules are a growing superfamily of 8-14 kDa proteins characterised by a conserved four cysteine motif. The chemokine superfamily can be divided into two main groups exhibiting characteristic structural motifs, the Cys-X-Cys (C-X-C) and Cys-Cys (C-C) families. These are distinguished on the basis of a single amino acid insertion between the NH-proximal pair of cysteine residues and sequence similarity.

The C-X-C chemokines include several potent chemoattractants and activators of neutrophils such as interleukin-8 (IL-8) and neutrophil-activating peptide 2 (AP-2).

The C-C chemokines include potent chemoattractants of monocytes and lymphocytes but not neutrophils such as human monocyte chemotactic proteins 1-3 (MCP-1, MCP-2 and MCP-3), RANTES (Regulated on Activation, Normal T Expressed and Secreted), eotaxin and the macrophage inflammatory proteins 1α and 1β (MIP-1α and MP-1β).

Studies have demonstrated that the actions of the chemokines are mediated by subfamilies of G protein-coupled receptors, among which are the receptors designated CCR1, CCR2, CCR2A, CCR2B, CCR3, CCR4, CCR5, CCR6, CCR7, CCR8, CCR9, CCR10, CXCR1, CXCR2, CXCR3 and CXCR4. These receptors represent good targets for drug development since agents which modulate these receptors would be useful in the treatment of disorders and diseases such as those mentioned above.

In accordance with the present invention, there is therefore provided a compound of general formula

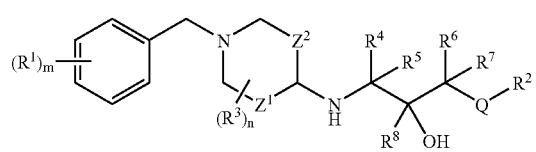

(I)

wherein
  m is 0, 1, 2 or 3;
  each $R^1$ independently represents halogen, cyano, nitro, carboxyl, hydroxyl, $C_3$-$C_6$ cycloalkyl, $C_1$-$C_6$ alkoxy, $C_1$-$C_6$ alkoxycarbonyl, $C_1$-$C_6$ haloalkyl, $C_1$-$C_6$ haloalkoxy, —$NR^9R^{10}$, $C_3$-$C_6$ cycloalkylamino, $C_1$-$C_6$ alkylthio, $C_1$-$C_6$ alkylcarbonyl, $C_1$-$C_6$ alkylcarbonylamino, sulphonamido (—$SO_2NH_2$), $C_1$-$C_6$ alkylsulphonyl, —$C(O)NR^{11}R^{12}$, —$NR^{13}C(O)$—$(NH)_pR^{14}$, phenyl, or $C_1$-$C_6$ alkyl optionally substituted by carboxyl or $C_1$-$C_6$ alkoxycarbonyl;
  p is 0 or 1;
  $Z^1$ represents a bond or a group $(CH_2)_q$ where q is 1 or 2;
  $Z^2$ represents a bond or a group $CH_2$, with the proviso that $Z^1$ and $Z^2$ do not both simultaneously represent a bond;
  Q represents an oxygen or sulphur atom or a group $CH_2$ or NH;
  $R^2$ represents a group

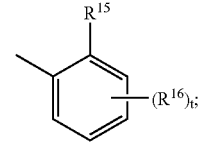

n is 0, 1 or 2;
  each $R^3$ independently represents a $C_1$-$C_6$ alkyl, $C_1$-$C_6$ alkoxycarbonyl, —$CH_2OH$ or carboxyl group;
  $R^4$, $R^5$, $R^6$ and $R^7$ each independently represent a hydrogen atom or a $C_1$-$C_6$ alkyl group, or $R^4$, $R^5$, $R^6$ and $R^7$ together represent a $C_1$-$C_4$ alkylene chain linking the two carbon atoms to which they are attached to form a 4 to 7-membered saturated carbocycle, or $R^5$, $R^6$ and $R^7$ each represent a hydrogen atom and $R^4$ and $R^8$ together with the carbon atoms to which they are attached form a 5- to 6-membered saturated carbocycle;
  $R^8$ represents a hydrogen atom, a $C_1$-$C_6$ alkyl group or is linked to $R^4$ as defined above;
  $R^9$ and $R^{10}$ each independently represent a hydrogen atom or a $C_1$-$C_6$ alkyl group, or $R^9$ and $R^{10}$ together with the nitrogen atom to which they are attached form a 4- to 7-membered saturated heterocycle;
  $R^{11}$ and $R^{12}$ each independently represent a hydrogen atom or a $C_1$-$C_6$ alkyl group optionally substituted by $C_1$-$C_6$ alkoxycarbonyl;
  $R^{13}$ represents a hydrogen atom or a $C_1$-$C_6$ alkyl group;
  $R^{14}$ represents a hydrogen atom, or a $C_1$-$C_6$ alkyl group optionally substituted by carboxyl, $C_1$-$C_6$ alkoxy or $C_1$-$C_6$ alkoxycarbonyl;
  $R^{15}$ represents carboxyl, $C_1$-$C_6$ alkoxy, $C_1$-$C_6$ alkylcarbonyl, $C_1$-$C_6$ alkoxycarbonyl, $C_1$-$C_6$ alkoxycarbonyl$C_1$-$C_6$ allyl or a group —$NR^{17}R^{18}$, —$NHSO_2CH_3$, —$C(O)NR^{17}R^{18}$, —$NHC(O)NR^{17}R^{18}$, —$OC(O)NR^{17}R^{18}$, —$OCH_2C(O)NR^{17}R^{18}$, —$NHC(O)OR^{19}$ or —$NHC(O)R^{20}$;
  t is 0, 1, 2 or 3;
  each $R^{16}$ independently represents halogen, cyano, nitro, carboxyl, hydroxyl, $C_3$-$C_6$ cycloalkyl, $C_1$-$C_6$ alkoxy, $C_1$-$C_6$ alkoxycarbonyl, $C_1$-$C_6$ haloalkyl, $C_1$-$C_6$ haloalkoxy, —$NR^{21}R^{22}$, $C_3$-$C_6$ cycloalkylamino, $C_1$-$C_6$ alkylthio, $C_1$-$C_6$ alkylcarbonyl, $C_1$-$C_6$ alkylcarbonylamino, sulphonamido (—$SO_2NH_2$), $C_1$-$C_6$ alkylsulphonyl, —$C(O)NR^{23}R^{24}$, —$NR^{25}C(O)(NH)_vR^{26}$, phenyl, or $C_1$-$C_6$ alkyl optionally substituted by carboxyl or $C_1$-$C_6$ alkoxycarbonyl;
  $R^{17}$ and $R^{18}$ each independently represent a hydrogen atom, or a $C_1$-$C_6$ alkyl group optionally substituted by carboxyl or $C_1$-$C_6$ alkoxycarbonyl, or $R^{17}$ and $R^{18}$ together with the nitrogen atom to which they are attached form a 4 to 7-membered saturated heterocycle;
  $R^{19}$ represents a hydrogen atom, or a $C_1$-$C_6$ alkyl group optionally substituted by carboxyl or $C_1$-$C_6$ alkoxycarbonyl;

$R^{20}$ represents a group $C_1$-$C_6$ alkyl, $C_2$-$C_6$ alkenyl, $C_3$-$C_6$ cycloalkyl, adamantyl, $C_5$-$C_6$ cycloalkenyl, phenyl or a saturated or unsaturated 5- to 10-membered heterocyclic ring system comprising at least one heteroatom selected from nitrogen, oxygen and sulphur, each of which may be optionally substituted by one or more substituents independently selected from nitro, hydroxyl, oxo, halogen, carboxyl $C_1$-$C_6$ alkyl, $C_1$-$C_6$ alkoxy, $C_1$-$C_6$alkylthio, $C_1$-$C_6$ alkylcarbonyl, $C_1$-$C_6$ alkoxycarbonyl, phenyl and —NHC(O)—$R^{27}$;

$R^{21}$ and $R^{22}$ each independently represent a hydrogen atom or a $C_1$-$C_6$ alkyl group, or $R^{21}$ and $R^{22}$ together with the nitrogen atom to which they are attached form a 4 to 7-membered saturated heterocycle;

$R^{23}$ and $R^{24}$ each independently represent a hydrogen atom or a $C_1$-$C_6$ alkyl group optionally substituted by $C_1$-$C_6$ alkoxycarbonyl;

v is 0 or 1;

$R^{25}$ represents a hydrogen atom or a $C_1$-$C_6$ alkyl group;

$R^{26}$ represents a hydrogen atom, or a $C_1$-$C_6$ alkyl group optionally substituted by carboxyl, $C_1$-$C_6$ alkoxy or $C_1$-$C_6$ alkoxycarbonyl; and $R^{27}$ represents a $C_1$-$C_6$ alkyl, amino (—$NH_2$) or phenyl group;

or a pharmaceutically acceptable salt or solvate thereof.

In the context of the present specification, an alkyl substituent group or an alkyl moiety in a substituent group may be linear or branched. When $R^9$ and $R^{10}$ (or $R^{17}$ and $R^{18}$, or $R^{21}$ and $R^{22}$) represent a saturated heterocycle, it should be understood that the only heteroatom present is the nitrogen atom to which $R^9$ and $R^{10}$ (or $R^{17}$ and $R^{18}$, or $R^{21}$ and $R^{22}$) are attached. In the definition of $R^{20}$, it should be noted that the saturated or unsaturated 5- to 10-membered heterocyclic ring system may be aliphatic or aromatic.

The integer m is preferably 1 or 2.

Each $R^1$ independently represents halogen (e.g. chlorine, fluorine, bromine or iodine), cyano, nitro, carboxyl, hydroxyl, $C_3$-$C_6$ cycloalkyl (cyclopropyl, cyclobutyl, cyclopentyl or cyclohexyl), $C_1$-$C_6$, preferably $C_1$-$C_4$, alkoxy (e.g. methoxy, ethoxy, n-propoxy or n-butoxy), $C_1$-$C_6$, preferably $C_1$-$C_4$, alkoxycarbonyl (e.g. methoxycarbonyl or ethoxycarbonyl), $C_1$-$C_6$, preferably $C_1$-$C_4$, haloalkyl (e.g. trifluoromethyl), $C_1$-$C_6$, preferably $C_1$-$C_4$, haloalkoxy (e.g. trifluoromethoxy), —$NR^9R^{10}$, $C_3$-$C_6$, cycloalkylamino (e.g. cyclopropylamino, cyclobutylamino, cyclopentylamino or cyclohexylamino), $C_1$-$C_6$, preferably $C_1$-$C_4$, alkylthio (e.g. methylthio or ethylthio), $C_1$-$C_6$, preferably $C_1$-$C_4$, alkylcarbonyl (e.g. methylcarbonyl, ethylcarbonyl, n-propylcarbonyl, isopropylcarbonyl, n-butylcarbonyl, n-pentylcarbonyl or n-hexylcarbonyl), $C_1$-$C_6$, preferably $C_1$-$C_4$, alkylcarbonylamino (e.g. methylcarbonylamino or ethylcarbonylamino), sulphonamido, $C_1$-$C_6$, preferably $C_1$-$C_4$, alkylsulphonyl (e.g. methylsulphonyl, ethylsulphonyl, n-propylsulphonyl, isopropylsulphonyl, n-butylsulphonyl, n-pentylsulphonyl or n-hexylsulphonyl), —C(O)$NR^{11}R^{12}$, —$NR^{13}$C(O)—$(NH)_p$ $R^{14}$, phenyl, or $C_1$-$C_6$, preferably $C_1$-$C_4$, allyl (e.g. methyl, ethyl, n-propyl, isopropyl, n-butyl, isobutyl, tert-butyl, n-pentyl or n-hexyl) optionally substituted by carboxyl or $C_1$-$C_6$, preferably $C_1$-$C_4$, alkoxycarbonyl (e.g. methoxycarbonyl or ethoxycarbonyl).

Most preferably, each $R^1$ independently represents halogen particularly chlorine or fluorine), cyano, nitro, $C_1$-$C_6$ alkoxy (especially methoxy), $C_1$-$C_6$ alkylcarbonyl (especially methylcarbonyl) or $C_1$-$C_6$ alkylcarbonylamino (particularly methylcarbonylamino). Each $R^1$ especially represents a halogen atom.

Q preferably represents an oxygen atom.

Each $R^3$ independently represents a $C_1$-$C_6$, preferably $C_1$-$C_4$, alkyl (e.g. methyl, ethyl, n-propyl, isopropyl, n-butyl, isobutyl, tert-butyl, n-pentyl or n-hexyl), $C_1$-$C_6$, preferably $C_1$-$C_4$, alkoxycarbonyl (e.g. methoxycarbonyl or ethoxycarbonyl), —$CH_2OH$ or carboxyl group. It is preferred that $R^3$ represents a methyl, methoxycarbonyl, ethoxycarbonyl, —$CH_2OH$ or carboxyl group.

$R^4$, $R^5$, $R^6$ and $R^7$ each independently represent a hydrogen atom or a $C_1$-$C_6$, preferably $C_1$-$C_4$, allyl (e.g. methyl, ethyl, n-propyl, isopropyl, n-butyl, isobutyl, tert-butyl, n-pentyl or n-hexyl), or $R^4$, $R^5$, $R^6$ and $R^7$ together represent a $C_1$-$C_4$ alkylene chain linking the two carbon atoms to which they are attached to form a 4 to 7-membered saturated carbocycle (e.g. cyclohexyl or preferably cyclopentyl), or $R^5$, $R^6$ and $R^7$ each represent a hydrogen atom and $R^4$ and $R^8$ together with the carbon atoms to which they are attached form a 5- to 6-membered saturated carbocycle (preferably cyclopentyl).

$R^8$ represents a hydrogen atom, a $C_1$-$C_6$, preferably $C_1$-$C_4$, alkyl group (e.g. methyl, ethyl, n-propyl, isopropyl, n-butyl, isobutyl, tert-butyl, n-pentyl or n-hexyl) or is linked to $R^4$ as defined above.

$R^9$ and $R^{10}$ each independently represent a hydrogen atom or a $C_1$-$C_6$, preferably $C_1$-$C_4$, alkyl group (e.g. methyl, ethyl, n-propyl, isopropyl, n-butyl, isobutyl, tert-butyl, n-pentyl or n-hexyl), or $R^9$ and $R^{10}$ together with the nitrogen atom to which they are attached form a 4 to 7-membered saturated heterocycle (preferably pyrrolidinyl or piperidinyl).

$R^{11}$ and $R^{12}$ each independently represent a hydrogen atom or a $C_1$-$C_6$, preferably $C_1$-$C_4$, alkyl group (e.g. methyl, ethyl, n-propyl, isopropyl, n-butyl, isobutyl, tert-butyl, n-pentyl or n-hexyl) optionally substituted by a $C_1$-$C_6$, preferably $C_1$-$C_4$, alkoxycarbonyl substituent group.

$R^{13}$ represents a hydrogen atom or a $C_1$-$C_6$, preferably $C_1$-$C_4$, alkyl group (e.g. methyl, ethyl, n-propyl, isopropyl, n-butyl, isobutyl, tert-butyl, n-pentyl or n-hexyl).

$R^{14}$ represents a hydrogen atom, or a $C_1$-$C_6$, preferably $C_1$-$C_4$, alkyl group (e.g. methyl, ethyl, n-propyl, isopropyl, n-butyl, isobutyl, tert-butyl, n-pentyl or n-hexyl) optionally substituted by carboxyl, $C_1$-$C_6$, preferably $C_1$-$C_4$, alkoxy or $C_1$-$C_6$, preferably $C_1$-$C_4$, alkoxycarbonyl.

$R^{15}$ represents carboxyl, $C_1$-$C_6$, preferably $C_1$-$C_4$, alkoxy (e.g. methoxy, ethoxy, n-propoxy or n-butoxy), $C_1$-$C_6$, preferably $C_1$-$C_4$, alkylcarbonyl (e.g. methylcarbonyl, ethylcarbonyl, n-propylcarbonyl, isopropylcarbonyl, n-butylcarbonyl, n-pentylcarbonyl or n-hexylcarbonyl), $C_1$-$C_6$, preferably $C_1$-$C_4$, alkoxycarbonyl (e.g. methoxycarbonyl or ethoxycarbonyl), $C_1$-$C_6$ alkoxycarbonyl$C_1$-$C_6$ alkyl, preferably $C_1$-$C_4$ alkoxycarbonyl$C_1$-$C_4$ alkyl (e.g. methoxycarbonylmethyl or methoxycarbonylethyl), or a group —$NR^{17}R^{18}$, —$NHSO_2CH_3$, —C(O)$NR^{17}R^{18}$, —NHC(O)$NR^{17}R^{18}$, —OC(O)$NR^{17}R^{18}$, —$OCH_2$C(O)$NR^{17}R^{18}$, —NHC(O)$OR^{19}$ or —NHC(O)$R^{20}$.

It is preferred that $R^{15}$ represents $C_1$-$C_4$ alkoxy (especially methoxy), $C_1$-$C_4$ alkylcarbonyl (especially methylcarbonyl or ethylcarbonyl), $C_1$-$C_4$ alkoxycarbonyl$C_1$-$C_4$ alkyl (particularly methoxycarbonylmethyl or methoxycarbonylethyl), —C(O)$NR^{17}R^{18}$, —$NHSO_2CH_3$, —NHC(O)$NR^{17}R^{18}$ or, especially, —NHC(O)$R^{20}$.

Each $R^{16}$ independently represents halogen (e.g. chlorine, fluorine, bromine or iodine), cyano, nitro, carboxyl, hydroxyl, $C_3$-$C_6$ cycloalkyl (cyclopropyl, cyclobutyl, cyclopentyl or cyclohexyl), $C_1$-$C_6$, preferably $C_1$-$C_4$, alkoxy (e.g. methoxy, ethoxy, n-propoxy or n-butoxy), $C_1$-$C_6$, preferably $C_1$-$C_4$, alkoxycarbonyl (e.g. methoxycarbonyl or ethoxycarbonyl), $C_1$-$C_6$, preferably $C_1$-$C_4$, haloalkyl (e.g. trifluoromethyl), $C_1$-$C_6$, preferably $C_1$-$C_4$, haloalkoxy (e.g. trifluoromethoxy), —NR²¹R²², $C_3$-$C_6$ cycloalkylamino (e.g. cyclopropylamino, cyclobutylamino, cyclopentylamino or cyclohexylamino), $C_1$-$C_6$, preferably $C_1$-$C_4$, alkylthio (e.g. methylthio or ethylthio), $C_1$-$C_6$, preferably $C_1$-$C_4$, alkylcarbonyl (e.g. methylcarbonyl, ethylcarbonyl, n-propylcarbonyl, isopropylcarbonyl, n-butylcarbonyl, n-pentylcarbonyl or n-hexylcarbonyl), $C_1$-$C_6$, preferably $C_1$-$C_4$, alkylcarbonylamino (e.g. methylcarbonylamino or ethylcarbonylamino), sulphonamido, $C_1$-$C_6$, preferably $C_1$-$C_4$, alkylsulphonyl (e.g. methylsulphonyl, ethylsulphonyl, n-propylsulphonyl, isopropylsulphonyl, n-butylsulphonyl, n-pentylsulphonyl or n-hexylsulphonyl), —C(O)NR²³R²⁴, —NR²⁵C(O)—(NH)$_v$ R²⁶, phenyl, or $C_1$-$C_6$, preferably $C_1$-$C_4$, alkyl (e.g. methyl, ethyl, n-propyl, isopropyl, n-butyl, isobutyl, tert-butyl, n-pentyl or n-hexyl) optionally substituted by carboxyl or $C_1$-$C_6$, preferably $C_1$-$C_4$, alkoxycarbonyl (e.g. methoxycarbonyl or ethoxycarbonyl).

Preferably, each R¹⁶ independently represents halogen (particularly chlorine or fluorine), cyano, $C_1$-$C_4$ alkoxy (especially methoxy), $C_1$-$C_4$ alkoxycarbonyl (especially methoxycarbonyl), $C_1$-$C_4$ haloalkyl (especially trifluoromethyl), $C_1$-$C_4$ alkylcarbonyl particularly methylcarbonyl), phenyl or $C_1$-$C_4$ alkyl (e.g. methyl or tert-butyl).

R¹⁷ and R¹⁸ each independently represent a hydrogen atom or a $C_1$-$C_6$, preferably $C_1$-$C_4$, alkyl group (e.g. methyl, ethyl, n-propyl, isopropyl, n-butyl, isobutyl, tert-butyl, n-pentyl or n-hexyl) optionally substituted by carboxyl or, more preferably, $C_1$-$C_6$, preferably $C_1$-$C_4$, alkoxycarbonyl, especially methoxycarbonyl, or R¹⁷ and R¹⁸ together with the nitrogen atom to which they are attached form a 4 to 7-membered saturated heterocycle (preferably pyrrolidinyl or piperidinyl).

R¹⁹ represents a hydrogen atom or a $C_1$-$C_6$, preferably $C_1$-$C_4$, alkyl group (e.g. methyl, ethyl, n-propyl, isopropyl, n-butyl, isobutyl, tert-butyl, n-pentyl or n-hexyl) optionally substituted by carboxyl or, more preferably, $C_1$-$C_6$, preferably $C_1$-$C_4$, alkoxycarbonyl, especially methoxycarbonyl.

R²⁰ represents a group $C_1$-$C_6$, preferably $C_1$-$C_5$, alkyl group (e.g. methyl, ethyl, n-propyl, isopropyl, n-butyl, isobutyl, tert-butyl, n-pentyl or n-hexyl), $C_2$-$C_6$, preferably $C_2$-$C_4$, alkenyl, $C_3$-$C_6$ cycloalkyl (cyclopropyl, cyclobutyl, cyclopentyl or cyclohexyl), adamantyl, $C_5$-$C_6$ cycloalkenyl, phenyl or a saturated or unsaturated 5- to 10-membered heterocyclic ring system comprising at least one heteroatom (e.g. one, two, three or four heteroatoms) selected from nitrogen, oxygen and sulphur, each of which may be optionally substituted by one or more. (e.g. one, two, three or four) substituents independently selected from nitro, hydroxyl, oxo, halogen (e.g. fluorine, chlorine, bromine or iodine), carboxyl, $C_1$-$C_6$, preferably $C_1$-$C_4$, alkyl (e.g. methyl, ethyl, n-propyl, isopropyl, n-butyl, isobutyl, tert-butyl, n-pentyl or n-hexyl), $C_1$-$C_6$, preferably $C_1$-$C_4$, alkoxy (e.g. methoxy, ethoxy, n-propoxy or n-butoxy), $C_1$-$C_6$, preferably $C_1$-$C_4$, alkylthio (e.g. methylthio or ethylthio), $C_1$-$C_6$, preferably $C_1$-$C_4$, alkylcarbonyl (e.g. methylcarbonyl, ethylcarbonyl, n-propylcarbonyl, isopropylcarbonyl, n-butylcarbonyl, n-pentylcarbonyl or n-hexylcarbonyl), $C_1$-$C_6$, preferably $C_1$-$C_4$, alkoxycarbonyl (e.g. methoxycarbonyl or ethoxycarbonyl), phenyl and —NHC(O)—R²⁷.

The saturated or unsaturated 5- to 10-membered heterocyclic ring system may be monocyclic or polycyclic (e.g. bicyclic) and may comprise up to four heteroatoms independently selected from nitrogen, oxygen and sulphur. Examples of ring systems that may be used include pyrrolidinyl, piperidinyl, pyrazolyl, thiazolidinyl, thienyl, isoxazolyl, thiadiazolyl, pyrrolyl, furanyl, thiazolyl, indolyl, quinolinyl, benzimidazolyl, triazolyl, tetrazolyl and pyridinyl.

R²¹ and R²² each independently represent a hydrogen atom or a $C_1$-$C_6$, preferably $C_1$-$C_4$, alkyl group (e.g. methyl, ethyl, n-propyl, isopropyl, n-butyl, isobutyl, tert-butyl, n-pentyl or n-hexyl), or R²¹ and R²² together with the nitrogen atom to which they are attached form a 4 to 7-membered saturated heterocycle (preferably pyrrolidinyl or piperidinyl).

R²³ and R²⁴ each independently represent a hydrogen atom or a $C_1$-$C_6$, preferably $C_1$-$C_4$, alkyl group (e.g. methyl, ethyl, n-propyl, isopropyl, n-butyl, isobutyl, tert-butyl, n-pentyl or n-hexyl) optionally substituted by a $C_1$-$C_6$, preferably $C_1$-$C_4$, alkoxycarbonyl substituent group.

R²⁵ represents a hydrogen atom or a $C_1$-$C_6$, preferably $C_1$-$C_4$, alkyl group (e.g. methyl, ethyl, n-propyl, isopropyl, n-butyl, isobutyl, tert-butyl, n-pentyl or n-hexyl).

R²⁶ represents a hydrogen atom, or a $C_1$-$C_6$, preferably $C_1$-$C_4$, alkyl group (e.g. methyl, ethyl, n-propyl, isopropyl, n-butyl, isobutyl, tert-butyl, n-pentyl or n-hexyl) optionally substituted by carboxyl, $C_1$-$C_6$, preferably $C_1$-$C_4$, alkoxy or $C_1$-$C_6$, preferably $C_1$-$C_4$, alkoxycarbonyl.

R²⁷ represents a $C_1$-$C_6$, preferably $C_1$-$C_4$, allyl group (e.g. methyl, ethyl, n-propyl, isopropyl, n-butyl, isobutyl tert-butyl, n-pentyl or n-hexyl), amino or phenyl group.

Preferred compounds of the invention include:

N-[2-(3-{[1-(3,4-dichlorobenzylpiperidinyl]aminohydroxypropoxy)phenyl]acetamide, N-[5-chloro-2-(3-{[1-(3,4-dichlorobenzyl)-4-piperidinyl]amino}-2-hydroxypropoxy)phenyl]acetamide, N-[2-(3-{[1-(3,4-dichlorobenzyl)-4-piperidinyl]amino}-2-hydroxypropoxy)-5-methylphenyl]acetamide, N-[4-(3-{[1-(3,4-dichlorobenzyl)-4-piperidinyl]amino}-2-hydroxypropoxy)[1,1'-biphenyl]-3-yl]acetamide, N-[3-acetyl-2-(3-{[1-(3,4-dichlorobenzyl)-4-piperidinyl]amino}-2-hydroxypropoxy)-5-methylphenyl]acetamide, N-[2-(3-1 [1-(3-dichlorobenzyl)-4-piperidinyl]amino}-2-hydroxypropoxy)-4-fluorophenyl]acetamide, N-[23-{[1-(3,4-dichlorobenzyl)-4-piperidinyl]amino}-2-hydroxypropoxy)-5-fluorophenyl]acetamide, N-[2-(3-{[1-(3,4-dichlorobenzyl)-4-piperidinyl]amino}-2-hydroxypropoxy)-5-cyanophenyl]acetamide, N-[2-(3-{[1-chlorobenzyl)-4-piperidinyl]amino}-2-hydroxypropoxy)phenyl]-acetamide, N-[2-(3-{[1-(chlorobenzyl)-4-piperidinyl]amino}-hydroxypropoxy)phenyl]-isobutyramide, N-[2-(3-{[1-(4-chlorobenzyl)-4-piperidinyl]amino}-2-hydroxypropoxy)phenyl]-2-2-dimethyl-propiomanide, N-[5-chloro-2-(3-{[1-(chlorobenzyl)-4-piperidinyl]amino}-2-hydroxypropoxy)phenyl]acetamide, N-[2-(3-{[1-(4-chlorobenzyl)-4-piperidinyl]amino}-2-hydroxypropoxy)-5-methylphenyl]acetamide, N-[2-(3-{[1-(4-chlorobenzyl)-4-piperidinyl]amino}-2-hydroxypropoxy)-4-methylphenyl]acetamide, N-[2-(3-{[1-(4-chlorobenzyl)-4-piperidinyl]amino}-2-hydroxypropoxy)-4-fluorophenyl]acetamide, N-[2-(3-{[1-(4-chlorobenzyl)-4-piperidinyl]amino}-2-hydroxypropoxy)-5-cyanophenyl]acetamide, N-(2-{[(2S)-3-({-[(4-Chlorophenyl)methyl]-4-piperidinyl}amino)-2-hydroxypropyl]oxy}phenyl)acetamide bi(trifluoroacetate), N-(2-{(2R)-3-[1-(4-Chloro-benzyl)-piperidin-4-ylamino]-2-hydroxy-2-methyl-propoxy}-phenyl)-acetamide, N-(2-{[3-({1-[(4-Chlorophenyl)methyl]-4-piperidinyl}amino)-2-hydroxy-2-methylpropyl]oxy}phenyl)acetamide, N-(2-{(2S)-3-[1-(4-Chloro-benzyl)-piperidin-4-ylamino]-2-hydroxy-2-methyl-propoxy}-phenyl)-acetamide,
N-{2-[((2S)-3-{[1-(4-Fluorobenzyl)₄-piperidinyl]amino}-2-hydroxypropyl)oxy]phenyl}acetamide,
N-{2-[((2S)-3-{[1-(4-Chlorobenzyl)-4-piperidinyl]amino}-2-hydroxypropyl)oxy]4-fluorophenyl}acetamide,
N-{4-fluoro-2-[((2S)-3-{[1-(4-fluorobenzyl)₄-piperidinyl]amino}-2-hydroxypropyl)oxy]phenyl}acetamide,
N-{2-[((2S)-3-{[(3S)-1-(4-Chlorobenzyl)pyrrolidinyl]amino}-2-hydroxypropyl)oxy]-4-fluorophenyl}acetamide,
N-{2-[((2S)-3-{[(3R)-1-(4-Chlorobenzyl)pyrrolidinyl]amino}-2-hydroxypropyl)oxy]-4-fluorophenyl}acetamide,
N-[2-(3-{[1-(4-Fluorobenzyl)-4-piperidinyl]amino}-2-hydroxy-2-methylpropoxy)phenyl]acetamide,
N-[2-(3-{[1-(4-Chlorobenzyl)-4-piperidinyl]amino}-2-hydroxy-2-methylpropoxy)-4-fluorophenyl]acetamide,
N-[4-Fluoro-2-(3-{[1-(4-fluorobenzyl)-4-piperidinyl]amino}-2-hydroxy-2-methylpropoxy)phenyl]acetamide,
N-[2-(3-{[1-(4-Chlorobenzyl)-4-piperidinyl]amino}-2-hydroxypropoxy)-4-methylphenyl]acetamide,
N-[2-(3-{[1-(4-Fluorobenzyl)-4-piperidinyl]amino}-2-hydroxypropoxy)-4-methylphenyl]acetamide,
N-[23-{[1-(4-Chlorobenzyl)-4-piperidinyl]amino}-2-hydroxypropoxy)phenyl]benzamide,
N-[2-(3-{[1-(4-Fluorobenzyl)-4-piperidinyl]amino}-2-hydroxypropoxy)phenyl]benzamide,
N-[2-(3-{[(3S)-1-(4-Chlorobenzyl)pyrrolidinyl]amino}-2-hydroxypropoxy)phenyl]benzamide,
N-[2-(3-{[(3R)-1-(4-Chlorobenzyl)pyrrolidinyl]amino}-2-hydroxypropoxy)phenyl]benzamide,
N-[2-(3-{[1-(4-Bromobenzyl)piperidinyl]amino}-2-hydroxypropoxy)phenyl]benzamide,
N-[2-(3-{[1-(4-Chlorobenzyl)-4-piperidinyl]amino}-2-hydroxy-2-methylpropoxy)phenyl]benzamide,
N-[2-(3-{[1-(4-Fluorobenzyl)-4-piperidinyl]amino}-2-hydroxy-2-methylpropoxy)phenyl]benzamide,
N-[23-{[(3R)-1-(4-Chlorobenzyl)pyrrolidinyl]amino}-2-hydroxy-2-methylpropoxy)phenyl]benzamide,
N-[2-(3-{[1-(4-Bromobenzyl)-Piperidinyl]amino}-2-hydroxy-2-methylpropoxy)phenyl]benzamide,
N-[2-(3-{[1-(4-Chlorobenzyl)-4-piperidinyl]amino}-2-hydroxypropoxy)-4-methoxyphenyl]acetamide,
N-[23-{[1-(Chlorobenzyl)-4-piperidinyl]amino}-2-hydroxypropoxy)-6-fluorophenyl]acetamide,
N-[2-Fluoro-6-(3-{[1-(4-fluorobenzyl)-4-piperidinyl]amino}-2-hydroxypropoxy)phenyl]acetamide,
2-(3-{[1-(4-Chlorobenzyl)-4-piperidinyl]amino}-2-hydroxy-2-methylpropoxy)-N-methylbenzamide,
N-(2-{3-[1-(3,4-Dichloro-benzyl)-piperidin-4-ylamino]-2-hydroxy-propoxy}-phenyl)-benzamide,
N-(2-{3-[1-(3-Chloro-4-fluoro-benzyl)-piperidin-4-ylamino]-2-hydroxy-propoxy}-phenyl)-benzamide,
N2-{3-[1-(3,4-Difluoro-benzyl)-piperidin-4-ylamino-2-hydroxy-propoxy}-phenyl)-benzamide,
N-(2-{3-[1-(3,4-Dichloro-benzyl)-piperidin-4-ylamino]-2-hydroxy-propoxy}-6-methyl-phenyl)-acetamide,
N-(2-{3-[1-(4-Fluoro-benzyl)-piperidin-4-ylamino]-2-hydroxy-propoxy}-6-methyl-phenyl)-acetamide,
N-(2-{3-[1-(4-Bromo-benzyl)-piperidin-4-ylamino]-2-hydroxy-2-methyl-propoxy}-phenyl)-acetamide,
N-(2-{3-[1-(3,4-Dichloro-benzyl)-piperidin-4-ylamino]-2-hydroxy-2-methyl-propoxy}-phenyl)-acetamide, N-(2-{3-[1-(3-Chloro-4-fluoro-benzyl)-piperidin-4-ylamino]-2-hydroxy-2-methyl-propoxy}-phenyl)-acetamide,
N-(2-{3-[1-(3,4-Difluoro-benzyl)-piperidin-4-ylamino]-2-hydroxy-2-methyl-propoxy}-phenyl)-acetamide,
2-{3-[1-(4-Bromo-benzyl)-piperidin-4-ylamino]-2-hydroxy-propoxy}-N-methyl-benzamide,
2-{3-[1-(3,4-Dichloro-benzyl)-piperidin-4-ylamino]-2-hydroxy-propoxy}-N-methyl-benzamide,
2-{3-[1-(4-Chloro-benzyl)-piperidin-4-ylamino]-2-hydroxy-propoxy}-N-methyl-benzamide,
2-{3-[1-(4-Fluoro-benzyl)-piperidin-4-ylamino]-2-hydroxy-propoxy}-N-methyl-benzamide,
3,5-Dimethyl-1H-pyrrole-2-carboxylic acid (2-{3-[1-(4-bromo-benzyl)-piperidin-4-ylamino]-2-hydroxy-propoxy}-phenyl)-amide,
3,5-Dimethyl-1H-pyrrole-2-carboxylic acid (2-{3-[1-(3-chloro-benzyl)-piperidin-4-ylamino]-2-hydroxy-propoxy}-phenyl)-amide,
3,5-Dimethyl-1H-pyrrole-2-carboxylic acid (2-{3-[1-(3-fluoro-benzyl)-piperidin-4-ylamino]-2-hydroxy-propoxy}-phenyl)-amide,
N-(2-{3-[1-(4-Bromo-benzyl)-piperidin-4-ylamino]-2-hydroxy-propoxy}-phenyl)-acetamide,
N-(2-f{3-[1-(3-Chloro-4-fluoro-benzyl)-piperidin-4-ylamino]-2-hydroxy-propoxy}-phenyl)-acetamide,
N-(2-{3-[1-(3,4-Difluoro-benzyl)piperidin-4-ylamino]-2-hydroxy-propoxy}-phenyl)-acetamide, and
N-(2-{3-[1-(4-Fluoro-benzyl)-piperidin-4-ylamino]-2-hydroxy-propoxy}-phenyl)-acetamide.

The present invention further provides a process for the preparation of a compound of formula (I) as defined above which comprises
(a) reacting a compound of general formula,

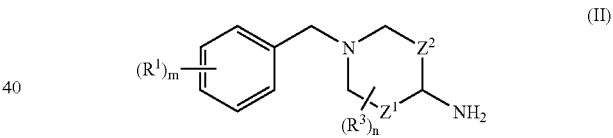

wherein m, n, Z¹, Z², R¹ and R³ are as defined in formula (I), with a compound of general formula

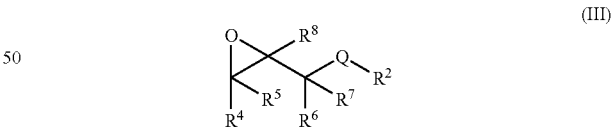

wherein Q, R², R⁴, R⁵, R⁶, R⁷ and R⁸ are as defined in formula (I); or
(b) reacting a compound of general formula

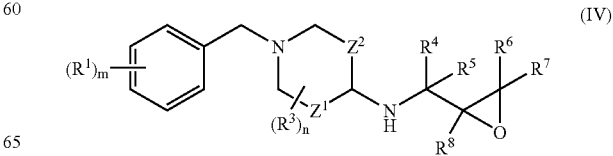

wherein m, n, $Z^1$, $Z^2$, $R^1$, $R^3$, $R^4$, $R^5$, $R^6$, $R^7$ and $R^8$ are as defined in formula (I), with a compound of general formula

$$L^1\text{-Q-}R^2 \quad (V)$$

wherein $L^1$ represents a hydrogen atom or a leaving group (e.g. Li when Q is $CH_2$) and Q and $R^2$ are as defined in formula (I); or (c) reacting a compound of general formula

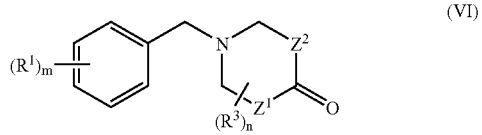

(VI)

wherein m, n, $Z^1$, $Z^2$, $R^3$ and $R^3$ are as defined in formula (I), with a compound of general formula

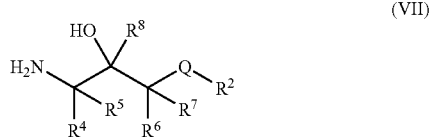

(VII)

wherein Q, $R^2$, $R^4$, $R^5$, $R^6$, $R^7$ and $R^8$ are as defined in formula (I);

and optionally after (a), (b) or (c) converting the compound of formula (I) to a further compound of formula (I) and/or forming a pharmaceutically acceptable salt or solvate of the compound of formula (I).

The process of the invention may conveniently be carried out in a solvent, e.g. an organic solvent such as an alcohol (e.g. methanol or ethanol), a hydrocarbon (e.g. toluene) or acetonitrile at a temperature of, for example, 15° C. or above such as a temperature in the range from 20 to 120° C.

Compounds of formulae (II), (III), (IV), (V), (VI) and (VII) are either commercially available, are well known in the literature or may be prepared easily using known techniques.

Compounds of formula (I) can be converted into further compounds of formula (I) using standard procedures. For example, a compound of formula (I) in which $R^{15}$ represents —NHC(O)$CH_3$ can be converted to a further compound of formula (I) in which $R^{15}$ represents —$NH_2$ by a hydrolysis reaction in the presence of hydrochloric acid.

It will be appreciated by those skilled in the art that in the process of the present invention certain functional groups such as hydroxyl or amino groups in the starting reagents or intermediate compounds may need to be protected by protecting groups. Thus, the preparation of the compounds of formula (I) may involve, at an appropriate stage, the removal of one or more protecting groups.

The protection and deprotection of functional groups is described in 'Protective Groups in Organic Chemistry', edited by J. W. F. McOmie, Plenum Press (1973) and 'Protective Groups in Organic Synthesis', 2nd edition, T. W. Greene and P. G. M. Wuts, Wiley-Interscience (1991).

The compounds of formula (I) above may be converted to a pharmaceutically acceptable salt or solvate thereof, preferably an acid addition salt such as a hydrochloride, hydrobromide, phosphate, acetate, fumarate, maleate, tartrate, citrate, oxalate, methanesulphonate or p-toluenesulphonate.

Compounds of formula (I) are capable of existing in stereoisomeric forms. It will be understood that the invention encompasses the use of all geometric and optical isomers of the compounds of formula (I) and mixtures thereof including racemates. The use of tautomers and mixtures thereof also form an aspect of the present invention. Preferred optical isomers are the (S)-enantiomers.

The compounds of formula (I) have activity as pharmaceuticals, in particular as modulators of chemokine receptor (especially MIP-1α chemokine receptor) activity, and may be used in the treatment of autoimmune, inflammatory, proliferative and hyperproliferative to diseases and immunologically-mediated diseases including rejection of transplanted organs or tissues and Acquired Immunodeficiency Syndrome (AIDS).

Examples of these conditions are:

(1) (the respiratory tract) airways diseases including chronic obstructive pulmonary disease (COPD) such as irreversible COPD; asthma, such as bronchial, allergic, intrinsic, extrinsic and dust asthma, particularly chronic or inveterate asthma (e.g. late asthma and airways hyper-responsiveness); bronchitis; acute, allergic, atrophic rhinitis and chronic rhinitis including rhinitis caseosa, hypertrophic rhinitis, rhinitis purulenta, rhinitis sicca and rhinitis medicamentosa; membranous rhinitis including croupous, fibrinous and pseudomembranous rhinitis and scrofoulous rhinitis; seasonal rhinitis including rhinitis nervosa (hay fever) and vasomotor rhinitis; sarcoidosis, farmer's lung and related diseases, fibroid lung and idiopathic interstitial pneumonia;

(2) (bone and joints) rheumatoid arthritis, seronegative spondyloarthropathies (including ankylosing spondylitis, psoriatic arthritis and Reiter's disease), Behcet's disease, Sjogren's syndrome and systemic sclerosis;

(3) (skin) psoriasis, atopical dermatitis, contact dermatitis and other eczmatous dermitides, seborrhoetic dermatitis, Lichen planus, Pemphigus, bullous Pemphigus, Epidermolysis bullosa, urticaria, angiodermas, vasculitides, erythemas, cutaneous eosinophilias, uveitis, Alopecia areata and vernal conjunctivitis;

(4) (gastrointestinal tract) Coeliac disease, proctitis, eosinopilic gastro-enteritis, mastocytosis, Crohn's disease, ulcerative colitis, food-related allergies which have effects remote from the gut, e.g., migraine, rhinitis and eczema;

(5) (other tissues and systemic disease) multiple sclerosis, atherosclerosis, Acquired Immunodeficiency Syndrome (AIDS), lupus erythematosus, systemic lupus, erythematosus, Hashimoto's thyroiditis, myasthenia gravis, type I diabetes, nephrotic syndrome, eosinophilia fascitis, hyper IgE syndrome, lepromatous leprosy, sezary syndrome and idiopathic thrombocytopenia pupura;

(6) (allograft rejection) acute and chronic following, for example, transplantation of kidney, heart, liver, lung, bone marrow, skin and cornea; and chronic graft versus host disease;

(7) cancers, especially non-small cell lung cancer (NSCLC) and squamous sarcoma;

(8) diseases in which angiogenesis is associated with raised chemokine levels (e.g. NSCLC); and (9) cystic fibrosis, stroke, re-perfusion injury in the heart, brain, peripheral limbs and sepsis.

Thus, the present invention provides a compound of formula (I), or a pharmaceutically-acceptable salt or solvate thereof, as hereinbefore defined for use in therapy.

In a further aspect, the present invention provides the use of a compound of formula (I), or a pharmaceutically acceptable salt or solvate thereof, as hereinbefore defined in the manufacture of a medicament for use in therapy.

In the context of the present specification, the term "therapy" also includes "prophylaxis" unless there are specific indications to the contrary. The terms "therapeutic" and "therapeutically" should be construed accordingly.

The invention also provides a method of treating an inflammatory disease in a patient suffering from, or at risk of, said disease, which comprises administering to the patient a therapeutically effective amount of a compound of formula (I), or a pharmaceutically acceptable salt or solvate thereof, as hereinbefore defined.

The invention still further provides a method of treating an airways disease in a patient suffering from, or at risk of; said disease, which comprises administering to the patient a therapeutically effective amount of a compound of formula (I), or a pharmaceutically acceptable salt or solvate thereof, as hereinbefore defined.

For the above-mentioned therapeutic uses the dosage administered will, of course, vary with the compound employed, the mode of administration, the treatment desired and the disorder indicated. The daily dosage of the compound of formula (I) may be in the range from 0.001 mg/kg to 30 mg/kg.

The compounds of formula (I) and pharmaceutically acceptable salts and solvates thereof may be used on their own but will generally be administered in the form of a pharmaceutical composition in which the formula (I) compound/salt/solvate (active ingredient) is in association with a pharmaceutically acceptable adjuvant, diluent or carrier. Depending on the mode of administration, the pharmaceutical composition will preferably comprise from 0.05 to 99% w (percent by weight), more preferably from 0.05 to 80% w, still more preferably from 0.10 to 70% w, and even more preferably from 0.10 to 50% w, of active ingredient, all percentages by weight being based on total composition.

The present invention also provides a pharmaceutical composition comprising a compound of formula (I), or a pharmaceutically acceptable salt or solvate thereof as hereinbefore defined, in association with a pharmaceutically acceptable adjuvant, diluent or carrier.

The invention further provides a process for the preparation of a pharmaceutical composition of the invention which comprises mixing a compound of formula (I), or a pharmaceutically acceptable salt or solvate thereof as hereinbefore defined, with a pharmaceutically acceptable adjuvant, diluent or carrier.

The pharmaceutical compositions may be administered topically (e.g. to the lung and/or airways or to the skin) in the form of solutions, suspensions, heptafluoroalkane aerosols and dry powder formulations; or systemically, e.g. by oral administration in the form of tablets, capsules, syrups, powders or granules, or by parenteral administration in the form of solutions or suspensions, or by subcutaneous administration or by rectal administration in the form of suppositories or transdermally.

The invention will now be further explained by reference to the following illustrative examples, in which $^1$H NMR spectra were recorded on Varian Unity Inova 400. The central solvent peak of chloroform-d ($\delta_H$ 7.27 ppm) were used as internal standard Low resolution mass spectra and accurate mass determination were recorded on a Hewlett-Packard 1100 LC-MS system equipped with APCI/ESI ionisation chambers. All solvents and commercial reagents were laboratory grade and used as received. The nomenclature used for the compounds was generated with ACD/UPAC Name Pro.

EXAMPLES 1-16

Starting Material:
1-(3,4-Dichlorobenzyl)-4-piperidinylamine i) Tert-Butyl 4-piperidinylcarbamate Di-tert-butyldicarbonate (11.6 g, 53.16 mmol) was added to a solution of 1-benzyl-4-piperidinamine (13.10 g, 68.84 mmol) in dichloromethane (100 ml) and triethylamine (2 ml) and the solution was stirred at room temperature for 2 hrs. Water was added to the solution and the organic layer was separated, dried over natrium sulphate, filtered and concentrated. The resulting residue was taken up into ethanol. Palladium hydroxide 20% (500 mg) was added to the solution and the mixture was hydrogenated (parr apparatus) over 50 psig hydrogen for 48 hrs. The mixture was filtered over a pad of celite. The solid was washed with two portions of hot ethanol and concentrated in vacuo to give 8.85 g product.

APCI-MS: m/z 0.201[M+]

$^1$HNMR (400 MHz, CD$_3$OD) δ 2.97-3.39(1H, m), 3 (2H, m), 2.55-2.62 (2H, m), 1.8-1.84 (2H,dd), 1.42 (9H, s), 1.27-1.37 (2H,m)

ii) 1-(3,4-Dichlorobenzyl)piperidinylamine 1,2-dichloro-4-(chloromethyl)benzene (390 mg, 1.99 mmol)) was added to a solution of tert-butyl 4-piperidinylcarbamate (400 mg, 2.0 mmol) in DMF (25 ml) and triethylamine (2 ml). The solution was stirred at room temperature for 3 hrs and then concentrated in vacuo. To the solution of the solid in dichloromethane was added (30 ml) trifluoroacetic acid (6 ml) was added and stirred at room temperature for 2 hrs. The solution was diluted with dichloromethane and washed with two portions of water. The combined water washings were treated with 2M NaOH to pH 10 and extracted with ether. The ether was dried (Na$_2$SO$_4$), filtered and evaporated to leave a yellow residue (300 mg, 1.16 mmol).

APCI-MS: m/z 259[MH+]

$^1$HNMR (400 MHZ, CD$_3$OD) δ 7.41(1H, d), 7.36 (1H, br d), 7.13 (1H, dd), 3.42 (2H, s), 2.97-3.01 (1H, m), 3 (2H, m), 2.55-2.62 (2H, m), 1.41-1.55 (2H,dd), 1.31-1.54 (2H,m)

Example 1

N-[2-(3-{[1-(3,4-dichlorobenzylpiperidinyl]amino-hydroxypropoxy)phenyl]acetamide The mixture of N-Acetyl-2-(2,3-epoxypropoxy)aniline (120 mg, 0.58 mmol) and the above starting material (150 mg, 0.58 mmol) in ethanol (10 ml 99.5%) was refluxed for 3 hrs. The solvent distilled off under reduced pressure, the resulting residue was purified by silica gel column chromatography (eluant: dichloromethane/methanol 15:1) to give 108 mg of the title compound as a gum. Addition of 1.0M ethereal HCl solution gave a white solid product.

APCI-MS: m/z 466[MH$^+$].

$^1$HNMR (400 MHz, CD$_3$OD) δ 8.0 (1H, dd,), 7.5 (1H, d), 7.45 (1H d), 7.23 (1H, dd), 6.89-7.08 (4H, m), 4.15 (1H, m), 3.9-4.1 (2H, m), 3.40 (2H, S), 2.97-3.11 (1H, m), 3 (2H, m), 2.55-2.68 (2H, m), 1.39-1.55 (2H,dd), 1.31-1.44 (2H,m), 2.17 (3H, s).

The following compounds were synthesised by methods analogous to the method described in Example 1.

Example 2

N-[5-chloro-2-(3-{[1-(3,4-dichlorobenzyl)-4-piperidinyl]amino}-2-hydroxypropoxy)phenyl]acetamide APCI-MS: m/z 500[MH$^+$]

Example 3

N-[2-(3-{[1-(3,4-dichlorobenzyl)-4-piperidinyl]amino}-2-hydroxypropoxy)-5-methylphenyl]acetamide APCI-MS: m/z 480[MH$^+$]

Example 4

N-[4-(3-{[1-(3,4-dichlorobenzyl)-4-piperidinyl]amino}-2-hydroxypropoxy)[1,1'-biphenyl]-3-yl]acetamide APCI-MS: m/z 542[MH$^+$]

Example 5

N-[3-acetyl-2-(3-{[1-(3,4-dichlorobenzyl)-4-piperidinyl]amino}-2-hydroxypropoxy)-5-methylphenyl]acetamide APCI-MS: m/z 522[MH$^+$]

Example 6

N-[2-(3-{[1-(3,4-dichlorobenzyl)-4-piperidinyl]amino}-2-hydroxypropoxy)-4-fluorophenyl]acetamide APCI-MS: m/z 484[MH$^+$]

Example 7

N-[2-(3-{[1-(3,4-dichlorobenzyl)-4-piperidinyl]amino}-2-hydroxypropoxy)-5-fluorophenyl]acetamide APCI-MS: m/z 484[MH$^+$]

Example 8

N-[2-(3-{[1-(3,4-dichlorobenzyl)-4-piperidinyl]amino}-2-hydroxypropoxy)-5-cyanophenyl]acetamide APCI-MS: m/z 491[MH$^+$]

Example 9

N-[2-(3-{[1-(4-chlorobenzyl)-4-piperidinyl]amino}-2-hydroxypropoxy)phenyl]-acetamide APCI-MS: m/z 432[MH$^+$]

Example 10

N-[2-(3-{[1-(4-chlorobenzyl)-4-piperidinyl]amin0}-hydroxypropoxy)phenyl]-isobutyramide APCI-MS: m/z 460[MH$^+$]

Example 11

N-[2-(3-{[1-(4-chlorobenzyl)-4-piperidinyl]amino}-2-hydroxypropoxy)phenyl]-2-2-dimethyl-propiomanide APCI-MS: m/z 474[MH$^+$]

Example 12

N-[5-chloro-2-(3-{[1-(4-chlorobenzyl)-4-piperidinyl]amino}-2-hydroxypropoxy)phenyl]acetamide APCI-MS: m/z 466[MH$^+$]

Example 13

N-[2-(3-{[1-(4-chlorobenzyl)-4-piperidinyl]amino}-2-hydroxypropoxy)-5-methylphenyl]acetamide APCI-MS: m/z 446[MH$^+$]

Example 14

N-[2-(3-{[1-(4-chlorobenzyl)-4-piperidinyl]amino}-2-hydroxypropoxy)-4-methylphenyl]acetamide APCI-MS: m/z 446[MH$^+$]

Example 15

N-[2-(3-{[1-(4-chlorobenzyl)-4-piperidinyl]amino}-2-hydroxypropoxy)-4-fluorophenyl]acetamide APCI-MS: m/z 450[MH$^+$]

Example 16

N-[2-(3-{[1-(4-chlorobenzyl)-4-piperidinyl]amino}-2-hydroxypropoxy)-5-cyanophenyl]acetamide APCI-MS: m/z 457[MH$^+$]

STARTING MATERIALS FOR EXAMPLES 17 TO 63

Epoxide: A

N-{2-[(2S)Oxiranylmethoxy]phenyl}acetamide (2S)-2-[(2-nitrophenoxy)methyl]oxirane (1.17 g, 6 mmol) was dissolved in ethyl acetate (50 ml). Platinum on charcoal (0.50 g) was added, and the mixture was stirred in the atmosphere of hydrogen for 3 h at room temperature and atmospheric pressure. The catalyst was filtered and washed on the filter with ethyl acetate (10 ml). Acetic anhydride (1.23 g, 1.13 ml, 12 mmol) and ethyldi(i-propyl)amine (1.55 g, 2.05 ml, 12 mmol) were added to the solution. The reaction mixture was stirred at room temperature for 3 h, then washed with 1M NaOH (2×50 ml) and brine (2×50 ml), and dried with Na$_2$SO$_4$. Evaporation of the solvent and flash chromatography on silica gel with n-heptane/ethyl acetate (from 25 to 75%) afforded the title compound (0.74 g, 3.57 mmol, 60%) as colourless crystals.

¹H-NMR (400 MHz, CDCl₃): δ 8.36 (m, 1H), 7.89 (br. S, 1H), 6.8-7.0 (m, 3H), 4.35 (dd, 1H, J=2.5, J=11.3), 3.95 (dd, 1H, J=5.9, J=11.3), 3.39 (m, 1H), 2.95 (t, 1H, J=4.8), 2.78 (dd, 1H, J=2.7, J=4.8), 2.22 (s, 3H).

APCI-MS: m/z 208 [MH⁺]

Epoxide: B i) [(2R)-2-Methyloxiranyl]methyl-4-methylbenzene-sulfonate (S)-2-methyl-glycidol (0.10 g, 1.13 mmol), dimethylaminopyridine (0.5 mg, 3.8 µmol) in triethylamine (2 ml) was cooled on an ice bath and tosyl chloride (0.217 g, 1.14 mmol) was added in portions during 10 min. The flask was sealed and kept at −10° C. over night. The reaction mixture was evaporated and the residue was stirred with dry diethylether (3.5 ml). The solid was filtered off and washed with diethylether (3×1 ml). The filtrate was dried and concentrated in vacuo. The crude product was purified on silica (Heptane/EtOAc 1:2) to give 145 mg (53% O) of the subtitle compound.

¹H-NMR (400 MHz, CDCl₃): δ 7.80 (2H, d, J=8.4 Hz), 7.36 (2×, d, J=8.1 Hz), 4.04 (1H, d, J10.7 Hz), 3.95 (1H, d, J10.7 Hz), 2.70 (1H, d, J4.7 Hz), 2.64 (1H, d, J4.6 Hz), 2.46 (3H, s), 1.36 (3H, s).

ii) N-(2-{[(2R)-2-Methyloxiranyl]methoxy}phenyl)acetamide

To 2-acetamidophenol (90.5 mg, 0.598 mmol) and cesium carbonate (234 mg, 0.718 mmol) was added [(2R)-2-methyloxiranyl]methyl 4-methylbenzene-sulfonate (145 mg, 0.598 mmol) dissolved in DMF (1 ml). The mixture was stirred at room temperature for four hours and then partitioned between ethyl-acetate and water. After extraction the combined organic phases were dried and concentrated in vacuo. The residue was purified on silica (Heptane/EtOAc 3:1-2:1) to give 63 mg (48%) of the title compound.

¹H-NMR (400 MHz, CDCl₃): δ 8.38-8.31 (1H, m), 8.02 (1H, bs), 7.04-6.97 (2H, m), 6.93-6.86 (1H, m), 4.11 (1H, d, J10.9 Hz), 4.01 (1H, d, J10.9 Hz), 2.95 (1H, d, J4.7 Hz), 2.78 (1H, d, J4.7H), 2.21 (3H, s), 1.48 (3H, s).

Epoxide: C i) [(2S)-2-Methyloxiranyl]methyl-3-nitrobenzene-sulfonate

To an oven-dried 1000 ml three-necked flask was added powdered activated molecular sieves (8.0 g, 4 Å) and CH₂Cl₂ (440 ml, dried over molecular sieves). D-(−)-Diisopropyl tartrate (3.0 ml, 14.2 mmol) and 2-methyl-2-propan-1-ol (20 ml, 240 mmol) was added and the mixture was cooled to −20° C. Titanium tetraisopropoxide (3.5 ml, 11.9 mmol) was added with a few ml of CH₂Cl₂ and the mixture was stirred at −20° C. for 30 minutes. Cumene hydroperoxide (75 ml, approx 430 mmol) was added dropwise over 1.5 hours maintaining the temperature at −20° C. The mixture was stirred at this temperature over night. Trimethylphosphite (40 ml, 340 mmol) was added dropwise over 5 hours maintaining the temperature at −20° C. Triethylamine (50 ml, 360 mmol) and DMAP (3.48 g, 28.5 mmol) was added followed by a solution of 3-nitrobenzenesulphonyl chloride (47 g, 212 mmol) in CH₂Cl₂ (400 ml). The temperature was raised to −10° C. and the mixture was stirred at this temperature over night. After removing the external cooling, the reaction mixture was filtered through celite®. The organic phase was washed with 10% tartaric acid (500 ml), saturated NaHCO₃ (300 ml) and brine (300 ml). The organic phase was dried MgSO₄) and evaporated to give ca 150 g of a yellow oil. The crude material was chromatographed (1 kg silica, Heptane/EtOAc 100:0 to 50:50 gradually increased polarity) to give 48.8 g (84%) of the sub-title compound as a yellow oil. The compound was pure enough to use further without any additional purification.

¹H-NMR (400 Hz, CDCl₃): □ 8.79-8.75 (1H, m); 8.52 (1H, ddd, J 1.1 2.3 8.3 Hz); 8.25 (1H, ddd, J 1.1 1.8 7.8 Hz); 7.81 (1H, t, J=8.5 Hz); 4.28 (1H, d, J 11.3 Hz); 4.05 (1H, d, J 11.3 Hz); 2.73 (1H, d, J=4.4 Hz); 2.67 (1H, d, J=4.4 Hz); 1.56 (3H, s)

ii) N-(2-{[(2S)-2-Methyloxiranyl]methoxy}phenyl)acetamide

In a flask was added the compound obtained in a) (24.57 g, 90 mmol), 2-acetamido-phenol (13.59 g, 90 mmol), Cs₂CO₃ (35.1 g, 108 mmol, powdered anhydrous) and DMF (90 ml). The flask was sealed and the mixture was stirred with a magnetic stirrer at room temperature for 2 hours. A heavy precipitate was formed, and the starting materials were converted in 2 hours. The mixture was partitioned between EtOAc/water (400+400 ml). The organic phase was collected and the aqueous phase was washed with EtOAc (2×200 ml). The combined organic phases were washed with water (200 ml), 1M NaOH (2×200 ml) and brine (150 ml). The organic solution was dried over Na₂SO₄, and concentrated in vacuo after filtration. The crude material was purified on silica (Heptane/EtOAc 5:1 to 1:1, gradually increasing the polarity), eluting 18.5 g (92%) of the sub-title compound. The optical purity was 97.4%, according to chiral HPLC (Chiralpak™, iso-hexane/iso-propanol 95:5).

¹H-NMR (400 MHz, CDCl₃): □ 8.39-8.32 (1H, m); 8.00 (1H, bs); 7.05-6.97 (2H, m); 6.95-6.88 (1H, m); 4.12 (1H, d, AB, J 11.0 Hz); 4.02 (1H, d, AB, J 11.0 Hz); 2.96 (1H, d, J=4.6 Hz); 2.79 (1H, d, J 4.8 Hz); 2.22 (3H, s); 1.49 (3H, s)

Epoxide: D

N-{4-Fluoro-2-[(2S)oxiranylmethoxy]phenyl}acetamide was prepared from (2S)-2-[(5-fluoro-2-nitrophenoxy)methyl]oxirane according to the method described for Epoxide: A.

APCI-MS: m/z 226 [MH⁺]

¹H-NMR (400 MHz, CDCl₃): δ 8.30 (dd, 1H, J=5.2, J 9.0), 7.71 (br. S, 1H), 8.6-8.8 (m, 2H), 4.36 (dd, 1H, J=2.3, J=11.3), 3.90 (dd, 1H, J=6.3, J=11.3), 3.40 (m, 1H), 2.97 (t, 1H, J=4.4), 2.78 (dd, 1H, J=2.7, J=4.8), 2.21 (s, 3H).

Epoxide: E

N-{2-[(2-Methyl-2-oxiranyl)methoxy]phenyl}benzamide

A mixture of N-(2-hydroxyphenyl)benzamide (159 mg; 0.75 mmol), 2-(chloromethyl)-2-methyloxirane (1.60 g, 15 mmol), and benzyltriethylammonium chloride (27 mg, 0.12 mmol) was stirred at 70-75° C. for 6 h After cooling to room temperature, water (2 ml) was added and the mixture was vigorously shaken. It was extracted with dichloromethane (2×5 ml), and the combined organic extracts were washed with aq. NaOH (2M, 5 ml) and water (10 ml). Drying with Na₂SO₄, evaporation of the solvent and flash chromatography on silica gel with n-heptane/ethyl acetate (ethyl acetate from 25 to 50%) afforded title compound as yellowish solid (131 mg, 0.46 mmol, 62%).

APCI-MS: m/z 284 [MH+]

¹H-NMR (400 MHz, CDCl₃): δ 8.68 (br. S, 1H), 8.54 (m, 1H), 7.94 (m, 2H), 7.4-7.6 (m, 3H), 7.07 (m, 2H), 6.92 (m, 1H), 4.19 (d, 1H, J=10.7), 4.06 (d, 1H, J 10.7), 2.92 (d, 1H, J=4.6), 2.78 (d, 1H, J=4.6).

Epoxide: F

N-Methyl-2-[(2-methyl-2-oxiranyl)methoxy]benzamide was prepared from 2-hydroxy-N-methylbenzamide (prepared according to Cohen et al, *J. Am. Chem. Soc.*, 1998, 20, 6277-6286.) according to the method described for N-{2-[(2-methyl-2-oxiranyl)methoxy]phenyl}benzamide.

APCI-MS: m/z 284 [MH+]

¹H-NMR (400 MHz, CDCl₃): δ 8.68 (br. S, 1H), 8.54 (m, 1H), 7.94 (m, 2H), 7.4-7.6 (m, 3H), 7.07 (m, 2H), 6.92 (m, 1H), 4.19 (d, 1H, J=10.7), 4.06 (d, 1H, J=10.7), 2.92 (d, 1H, J=4.6), 2.78 (d, 1H, J=4.6), 1.51 (s, 3H).

Epoxide: G

N-[4-Methyl-2-(2-oxiranylmethoxy)phenyl]acetamide

A mixture of N-(2-hydroxymethylphenyl)acetamide (10 g, 60 mmol), 2-(bromomethyl)oxirane (9.86 g, 72 mmol, 6.0 ml) and potassium carbonate (16.8 g, 120 mmol) in DMF (100 ml) was heated at 55° C. for 2 h. Then the reaction mixture was diluted with ethyl acetate and washed with aq. HCl (1.5%), aq sat. NaHCO₃, and brine. Evaporation of the solvent and flash chromatography on silica gel with n-heptane/ethyl acetate (ethyl acetate from 35 to 70%) afforded the title compound (5.65 g, 25 mmol, 43%).

APCI-MS: m/z 222 [MH+]

¹H-NMR (400 MHz, CDCl₃): δ 8.20 (d, 1H, J=8.2), 7.78 (br. s, 1H), 6.79 (d, 1H, J=8.2), 6.70 (s, 1H), 4.32 (dd, 1H, J=2.5, J=11.4), 3.93 (dd, 1H, J=5.9, J=11.4), 3.38 (m, 1H), 2.94 (t, 1H, J=4.8), 2.77 (dd, 1H, J=2.7, J=4.8), 2.29 (s, 3H), 2.19 (s, 3H).

Epoxide: H

N-[4-Methoxy-2-(2-oxiranylmethoxy)phenyl]acetamide

Was prepared from N-(2-hydroxy-4-methoxyphenyl)acetamide according to the method described for N-[4-methyl-2-(2-oxiranylmethoxy)phenyl]acetamide using cesium carbonate instead of potassium carbonate.

APCI-MS: m/z 238 [MH+]

¹H-NMR (400 MHz, CDCl₃): δ 8.20 (d, 1H, J=8.8), 7.62 (br. s, 1H), 6.4-6.6 (m, 2H), 6.70 (s, 1H), 4.32 (dd, 1H, J=2.5, J=11.3), 3.91 (dd, 1H, J=6.1, J=11.3), 3.77 (s, 3H), 3.37 (m, 1H), 2.94 (t, 1H, J=4.8), 2.76 (dd, 1H, J=2.7, J=4.8), 2.18 (s, 3H).

Epoxide: I i) 2-Amino-3-fluorophenol

To a stirred solution of 2,6-difluoronitrobenzene (1100 mg, 6.9 mmol) in dry methanol (20 ml) was added a solution of sodium (180 mg, 7.8 mmol) in dry methanol (8 ml). The solution was stirred overnight. After concentration, water was added and the solution was extracted with ether, dried over MgSO₄, filtered and concentrated to a yellow residue (870 mg, 5.08 mmol). To the solution of the yellow residue in dichloromethane (10 ml) boron tribromide (1M in dichloromethane, 10 ml) was added and stirred at room temperature overnight. Water was then added and the solution stirred for further 60 min. The organic phase was separated and the water phase was extracted with ether. The combined organic phase were dried over MgSO₄, filtered and concentrated in vacuo to give a brownish residue. The residue was taken up into ether and washed with 2M sodium hydroxide and water. The water and sodium hydroxide washings were combined and neutralised with 6M HCl and extracted with ether, dried over MgSO₄ and evaporated to give a yellow residue which was purified by flash chromatography on silica gel with EtOAc:Heptane: 1:3 as eluant to give the product (720 mg, 4.6 mmol) which was directly suspended with palladium-charcoal (140 mg) in water-ethanol (30 ml). Sodium borohydride (530 mg) was added over a period of 5 min and the suspension was stirred at room temperature (1 h). The catalyst was removed by filtration through a Celite pad. The filtrate was acidified with 6M hydrochloric acid to destroy any residual borohydride, neutralised with 2 M sodium hydroxide, and then extracted with ether. The ethereal extracts were dried over MgSO₄ and evaporated.

APCI-MS: m/z 128.2 [MH+]

ii)

N-[2-Fluoro-6-(2-oxiranylmethoxy)phenyl]acetamide

To a stirred solution of 2-amino-3-fluorophenol (300 mg, 2.36 mmol) in water-methanol (10 ml) acetic acid anhydride was added until all 2-amino-3-fluorophenol was consumed. The solution was concentrated to a residue of N-(2-fluoro-6-hydroxyphenyl) acetamide. To a mixture of N-(2-fluoro-6-hydroxyphenyl)acetamide (399 mg, 2.366 mmol) and potassium carbonate (652 mg, 4.72 mmol) in DMF (5 ml) epibromohydrin (388 mg, 2.8 mmol) was added and the mixture was stirred at 70° C. for 3 hr. Water and ethyl acetate were added, the organic phase separated, dried and concentrated. The resulting residue was purified by RP-HPLC (10-40% CH3CN) to give the desired product as a solid (242 mg, 1.08 mmol).

APCI-MS: m/z 226 μMH+]

¹H-NMR (400 MHz, CDCl₃): □ 7.15 (m, 1H), 6.87 (br. s, 1H), 6.6-6.8 (m, 2H), 4.30 (dd, 1H, J=2.3, J=11.3), 3.93 (dd, 1H, J=5.7, J=11.3), 3.34 (m, 1H), 2.91 (t, 1H, J=4.4), 2.75 (dd, 1H, J=2.8, J=4.8), 2.20 (br. s, 3H).

Epoxide: J

N-(2-Oxiranylmethoxy-phenyl)-benzamide

To a stirred solution of N-(2-Hydroxy-phenyl)-benzamide (0.81 g, 3.80 mmol), and cesium carbonate (1.61 g, 4.94 mmol) in acetontrile was added epibromohydrin (0.63 ml, 7.60 mmol). After 4 hours the reaction mixture was partitioned between dichloromethane and water. After evaporation of the organic solvent the residue was crystallised from petroleum ether and diethyl ether yielding (0.741 g, 73%).

APCI-MS: m/z 227[MH⁺]

¹H-NMR (400 MHz, CDCl₃): δ 8.65 (bs, 1H), 8.55 (bs, 1H), 7.94 (d, 2H), 7.53 (m, 3H), 7.08 (bs, 2H), 6.96 (bs, 1H), 4.42 (d, 1H), 4.02, (m, 1H), 3.41 (bs, 1H), 2.96 (s, 1H), 2.80 (s, 1H).

Epoxide: K

N-Methyl-2-oxiranylmethoxy-benzamide

To a solution of 2-Hydroxy-N-methyl-benzamide (0.5 g, 3.31 mmol prepared according to Cohen, Seth M et al J. Am. Chem. Soc., (1998), 120(25), 6277-6286.) and cesium carbonate (2.16 g, 6.62 mmol) in acetonitrile was added epibromohydrin (0.274 ml, 3.31 mmol). The mixture was heated at 50° C. for 2 hours and then after cooling to room temperature partitioned between water (50 ml) and dichloromethane (100 ml). The dichloromethane was dried and evaporated. Chromatography (EtOAc) gave 0.43 g (64%) of the product as a solid.

APCI-MS: m/z 208[MH$^+$]
$^1$H-NMR (400 MHz, CDCl$_3$): δ 8.20 (dd, 1H), 7.85 (bs, 1H), 7.42 (m, 1H), 7.11 (m, 1H), 6.95 (dd, 1H), 4.46 (dd, 1H), 4.11 (dd, 1H), 3.41 (m, 1H), 3.02 (d, 3H), 2.97 (t, 1H), 2.84 (dd, 1H).

Epoxide: L

N-(2-Methyl-6-oxiranylmethoxy-phenyl)-acetamide

A mixture of 3-methyl-2-acetamidophenol (0.165 g, 1 mmol), and epichlorohydrin (1.84 g, 20 mmol) was stirred at 70° C. to afford a clear solution. Triethylbenzylammonium chloride (0.15 g, 1 mmol) was then added and stirring was continued at 125° C. for 15 minutes. After cooling to room temperature 1M NaOH solution was added and the solution was extracted with dichloromethane. The organic extract was washed with water and dried. After evaporation of the dichloromethane the resulting brownish oil was purified through silica chromatography 50-70% EtOAc in heptane yielding the product as a colourless oil (0.12 g, 0.54 mmol).

APCI-MS: m/z 208[MH$^+$]

Epoxide: M 3,5 Dimethyl-1-H-pyrrole-2-carboxylic Acid (2-oxiranylmethoxy-phenyl)-acetamide The compound was prepared from 3,5 Dimethyl-1-H-pyrrole-2-carboxylic acid-(2-phenyl)-acetamide (300 mg, 1.3 mmol) analogously to that described for Epoxide: L.

APCI-MS: m/z 287 [MH$^+$]
$^1$H-NMR (400 MHz, CDCl$_3$): δ 8.46 (m,1H), 8.31 (m,1H), 6.99 (m,2H), 6.87 (m,1H), 5.85(m,1H), 4.34(m,1H), 3.92 (m, 1H), 3.36 (m,1H), 2.91 (m,2H), 2.71 (m,1H), 2.47 (m, 3H), 2.25 (m,3H).

(i) 3,5 Dimethyl-1-H-pyrrole-2-carboxylic Acid (2-phenyl)acetamide

2-Aminofenol (545 mg, 5 mmol), 3,5 dimethyl-1-H-pyrrole-2-carboxylic acid (ii) (695 mg, 5 mmol) and HATU (1900 mg, 5 mmol) were stirred in DMF (20 ml). Diisopropylethylamine was added to pH 8. The mixture was stirred overnight and then concentrated. The residue was purified on C18 (acetonitrile/water 10/90 to 40/60 with 0.5% trifluoroacetic acid) to give the title compound (550 mg, 48%).

APCI-MS: m/z 231 [MH$^+$]
$^1$H-NMR (400 MHz, CDCl$_3$): δ 9.22 (s,1H), 7.63 (s, 1H), 7.11(m, 2H), 7.03 (m, 1H), 6.88 (m,1H), 5.88 (s, 1H), 2.44 (s,1H), 2.24 (s,1H).

(ii) 3,5 Dimethyl-1-H-pyrrole-2-carboxylic Acid

To a solution of ethyl 3,5-dimethyl-2-pyrrolecarboxylate (Aldrich) (504 mg, 3 mmol) in THF/H$_2$O/MeOH (5:1:1, 30 ml) was added NaOH (480 mg, 12 mmol) in H$_2$O (12 ml). The mixture was stirred at 75° C. overnight. The homogeneous mixture was washed with ether. To the aqueous layer was added a saturated aqueous KHSO$_4$ solution until the pH was about 3. The solution was then extracted with dichloromethane. The extracts were dried over MgSO$_4$ and evaporated. The residue was purified on silica (ethylacetate/methanol 90/10) to give the title compound (375 mg, 90%).

$^1$H-NMR (400 MHz, CDCl$_3$): δ 8.75(s,1H), 5.83(s,1H), 2.25(s,1H), 2.38 (s,1H).

Amine: N 1-(4-Chlorobenzyl)-piperidineamine

1-Chloro-4-(chloromethyl)benzene (1.61 g, 10 mmol) was added to a stirred solution of tert-butyl 4-piperidinylcarbamate (2.02 g. 10.1 mmol) and triethylamine (10 ml) in dry DMF (100 ml). The solution was stirred at room temperature overnight and then the solvent was removed in vacuo. The residue was taken in dichloromethane (150 ml) and trifluoroacetic acid (30 ml) was added. After stirring at room temperature for 3 h, the solution was diluted with dichloromethane (150 ml), and extracted with water (2×150 ml). The pH of the combined aqueous extracts was adjusted to 10 by addition of 2 M NaOH. The solution was extracted with ether (3×100 ml). Drying with sodium sulfate and evaporation of the solvent afforded the title compound as yellowish oil (1.91 g, 8.5 mmol, 85%).

$^1$H-NMR (400 MHz, CDCl$_3$): δ 7.2-7.3 (m, 4H), 3.41 (s, 2H), 2.76 (m, 2H), 2.63 (m, 1H), 1.98 (m, 2H), 1.76 (m, 2H), 1.3-1.6 (m, 4H). APCI-MS: m/z 225 [MH$^+$]

Amine: O (3S)-1-(4-Chlorobenzyl)-3-pyrrolidinamine was prepared according the method described for Amine: N from tert-butyl (3S)pyrrolidinylcarbamate.

APCI-MS: m/z 211 [MH+]
$^1$H-NMR (400 MHz, CDCl$_3$): δ 7.2-7.3 (m, 4H), 5.55 (d, 2H), 3.49 (m, 1H), 2.66 (m 2H), 2.41 (m, 1H), 2.29 (dd, 1H), 2.18 (m, 1H), 1.68 (br. s, 2H), 1.48 (m, 1H).

Amine: P (3R)-1-(4-Chlorobenzyl)-3-pyrrolidinamine

Was prepared according the method described for Amine: N from tert-butyl (3R)pyrrolidinylcarbamate.

APCI-MS: m/z 211 [MH+]
$^1$H-NMR (400 MHz, CDCl$_3$): δ 7.2-7.3 (m, 4H), 5.55 (d, 2H), 3.49 (m, 1H), 2.66 (m, 2H), 2.41 (m, 1H), 2.29 (dd, 1H), 2.18 (m, 1H), 1.68 (br. s, 2H), 1.48 (m, 1H).

Amine: Q 3-(4-Chlorophenoxy)piperidine tert-Butyl 3-hydroxy-1-piperidinecarboxylate (1.85 g, 9.18 mmol, prepared according to Costa et al., *J. Med. Chem.* 1992, 35, 4334-4343) (1.85 g, 9.18 mmol) and triphenyl phosphine (2.41 g, 9.18 mmol) were dissolved in dry THF (25 ml) under nitrogen. The solution was cooled to 0° C. and a solution of 4-chlorophenol (1.18 g, 9.18 mmol) in dry THF (10 ml) was added followed by diethyl azodicarboxylate (1.60 g, 9.18 mmol, 1.45 ml). After 15 minutes the reaction mixture was allowed to warm to room temperature and stirred overnight. The solvent was removed in vacuo, the residue stirred with ether/n-heptane (1:2, 50 ml) mixture. The solid triphenyl phosphine oxide was filtered off, the solution washed with aq. NaOH (1M, 3×75 ml). Evaporation of the solvent and flash chromatography on silica gel with ethyl acetate/n-heptane (ethyl acetate from 5 to 25%) afforded the BOC-protected subtitle compound, which was dissolved in dichloromethane (20 ml). Trifluoroacetic acid (10 ml) was added, and the reaction mixture was stirred overnight at room temperature. The solution was concentrated in vacuo and the product was purified by flash chromatography on silica gel (MeOH/CHCl$_3$/NH$_3$, 100:100:1) to afford colourless oil (0.23 g, 12%).

APCI-MS: m/z 212 [MH+]

$^1$H-NMR (400 MHz, CDCl$_3$): δ 7.19 (m, 2H), 6.84 (m, 2H), 4.25 (m, 1H), 3.17 (m, 1H), 2.7-2.9 (m, 4H), 1.97 (m, 1H), 1.7-1.9 (m, 2H), 1.53 (m, 1H).

Amine: R 1-(4-Bromobenzyl)-4-piperidinylamine

To a solution of 4-bromo benzylbromide (1.0 g, 4.1 mmol) in dichloromethane (20 ml) and diisopropyletylamine (1 ml) was added tert-butyl 4-piperidinylcarbamate (1.0 g, 5.0 mmol). The solution was then stirred at room temperature over night. The solvent was evaporated and 25 ml of 50% TFA in dichloromethane was added to the resulting white solid. The mixture was then stirred at room temperature for 2 h and then evaporated to dryness. The resulting solid was dissolved in water and extracted with toluene. After removal of the toluene the water phase was made basic with 1M NaOH giving a pH of 13. The water phase was then extracted with dichloromethane 3 times and the combined extracts were dried and then evaporated to give the pure product as a slightly yellow oil (0.96 g, 3.6 mmol)

APCI-MS: m/z 269[M+]

$^1$H-NMR (400 MHz, CDCl$_3$): δ 7.42 (d, 2H), 7.18 (d, 2H), 3.43 (s, 2H), 2.78 (m, 3H), 2.43 (bs, 2H), 2.10 (t, 2H), 1.82 (m, 2H), 1.44 (m, 2H).

The following Amines (S, T, U) were synthesised by methods analogous to the method described for Amine R.

Amine: S 1-(3,4-Difluorobenzyl)-4-piperidinylamine

APCI-MS: m/z 227[MH$^+$]

Amine: T 1-(3-Chloro-4-fluorobenzyl)-4-piperidinylamine

APCI-MS: m/z 243[MH$^+$]

Amine: U 1-(4-Fluorobenzyl)piperidinylamine

APCI-MS: m/z 209[MH$^+$]

Example 17

N-(2-{[(2S)-3-({-[(4-Chlorophenyl)methyl]-4-piperidinyl}amino)-2-hydroxypropyl]oxy}phenyl) acetamide bi(trifluoroacetate)

A solution of 1-(4-chlorobenzyl)-piperidine amine (0.80 g, 3.57 mmol) and N-{2-[(2S)oxiranylmethoxy] phenyl}acetamide (0.74 g, 3.57 mmol) in ethanol (50 ml, 99.5%) was refluxed for 4 h. The solvent was distilled off under reduced pressure. The residue was purified by preparative HPLC (Kromasil C18 column; eluant: [acetonitrile+ 0.1% TFA/water+0.1% TFA]) to afford colourless solid (1.158 g, 1.75 mmol, 49%).

APCI-MS: m/z 432 [MH$^+$]

Example 18

N-(2-{(2R)-3-[1-(4-Chloro-benzyl)-piperidin-4-ylamino]-2-hydroxy-2-methyl-propoxy}-phenyl)-acetamide 1-(4-chlorobenzyl)-4-piperidinamine (62 mg, 0.276 mmol) and N-(2-{[(2R)-2-methyloxiranyl]methoxy}phenyl) acetamide (61 mg, 0.276 mmol) in ethanol (1.5 ml) was stirred in a sealed vial at 80° C. for 4 hours. The reaction mixture was diluted with water and purified by reversed phase HPLC to give 130 mg (70%) of the title compound as a ditrifluoroacetate after lyophilisation. The optical purity was determined to 86% ee, by chiral HPLC on a Chiralpak AD-column.

APCI-MS: m/z446.1 [M+]

Example 19

N-(2-{[3-({1-[(4-Chlorophenyl)methyl]-4-piperidinyl}amino)-2-hydroxy-2-methylpropyl] oxy}phenyl)acetamide Prepared by analogy to the method described in Example 18 from racemic epoxide.

APCI-MS: m/z 446.1 [M+]

Example 20

N-(2-{(2S)-3-[1-(4-Chloro-benzyl)-piperidin-4-ylamino]-2-hydroxy-2-methyl-propoxy}-phenyl)-acetamide Prepared according to the method described in Example 18 from N-(2-(((2S)-2-methyloxiranyl)methoxy)phenyl)acetamide, >98% yield was obtained.

APCI-MS: m/z 446.1 [M+]

General Procedure (Examples 21-43)

To a solution of the amine in EtOH (0.1 M, 0.2 ml) a solution of the epoxide in DMSO (0.1 M, 0.2 ml) was added The reaction mixture was heated at 80° C. for 24 h.

Example 21

N-{2-[((2S)-3-{[1-(4-Fluorobenzyl)-4-piperidinyl] amino}-2-hydroxypropyl)oxy]phenyl}acetamide APCI-MS: m/z 416 [MH+]

Example 22

N-{2-[((2S)-3-{[1-(4-Chlorobenzyl)-4-piperidinyl] amino}-2-hydroxypropyl)oxy]4-fluorophenyl}acetamide APCI-MS: m/z 450 [MH+]

Example 23

N-{4-fluoro-2-[((2S)-3-{[1-(4-fluorobenzyl)-4-piperidinyl]amino}-2-hydroxypropyl)oxy] phenyl}acetamide APCI-MS: m/z 434[MH+]

Example 24

N-{2-[((2S)-3-{[(3S)-1-(4-Chlorobenzyl)pyrrolidinyl]amino}-2-hydroxypropyl)oxy]-4-fluorophenyl}acetamide APCI-MS: m/z 436 [MH+]

Example 25

N-{2-[((2S)-3-{[(3R)-1-(4-Chlorobenzyl)pyrrolidinyl]amino}-2-hydroxypropyl)oxy]4-fluorophenyl}acetamide APCI-MS: m/z 436 [MH+]

Example 26

N-[2-(3-{[1-(4-Fluorobenzyl)-4-piperidinyl]amino}-2-hydroxy-2-methylpropoxy)phenyl]acetamide APCI-MS: m/z 430 [MH+]

Example 27

N-[2-(3-{[1-(4-Chlorobenzyl)-4-piperidinyl]amino}-2-hydroxy-2-methylpropoxy)-4-fluorophenyl]acetamide APCI-MS: m/z 464 [MH+]

Example 28

N-[4-Fluoro-2-(3-{[1-(4-fluorobenzyl)-4-piperidinyl]amino}-2-hydroxy-2-methylpropoxy)phenyl]acetamide APCI-MS: m/z 448 [MH+]

Example 29

N-[2-(3-{[1-(4-Chlorobenzyl)-4-piperidinyl]amino}-2-hydroxypropoxy)-4-methylphenyl]acetamide APCI-MS: m/z 446 [MH+]

Example 30

N-[2-(3-{[1-(4-Fluorobenzyl)-4-piperidinyl]amino}-2-hydroxypropoxy)-4-methylphenyl]acetamide APCI-MS: m/z 430 [MH+]

Example 31

N-[2-(3-{[1-(4-Chlorobenzyl)-4-piperidinyl]amino}-2-hydroxypropoxy)phenyl]benzamide APCI-MS: m/z 494 [MH+]

Example 32

N-[2-(3-{[1-(4-Fluorobenzyl)-4-piperidinyl]amino}-2-hydroxypropoxy)phenyl]benzamide APCI-MS: m/z 478 [MH+]

Example 33

N-[2-(3-{[(3S)-1-(4-Chlorobenzyl)pyrrolidinyl]amino}-2-hydroxypropoxy)phenyl]benzamide APCI-MS: m/z 480 [MH+]

Example 34

N-[2-(3-{[(3R)-1-(4-Chlorobenzyl)pyrrolidinyl]amino}-2-hydroxypropoxy)phenyl]benzamide APCI-MS: m/z 480 [MH+]

Example 35

N-[2-(3-{[1-(4-Bromobenzyl)-4-piperdinyl]amino}-2-hydroxypropoxy)phenyl]benzamide APCI-MS: m/z 540 [MH+]

Example 36

N-[2-(3-{[1-(4-Chlorobenzyl)-4-piperidinyl]amino}-2-hydroxy-2-methylpropoxy)phenyl]benzamide APCI-MS: m/z 508 [MH+]

Example 37

N-[2-(3-{[1-(4-Fluorobenzyl)-4-piperidinyl]amino}-2-hydroxy-2-methylpropoxy)phenyl]benzamide APCI-MS: m/z 492 [MH+]

Example 38

N-[2-(3-{[(3R)-1-(4-Chlorobenzyl)pyrrolidinyl]amino}-2-hydroxy-2-methylpropoxy)phenyl]benzamide APCI-MS: m/z 494 [MH+]

Example 39

N-[2-(3-{[1-(4-Bromobenzyl)-4-piperidinyl]amino}-2-hydroxy-2-methylpropoxy)phenyl]benzamide APCI-MS: m/z 554 [MH+]

Example 40

N-[2-(3-{[1-(4-Chlorobenzyl)-4-piperidinyl]amino}-2-hydroxypropoxy)-4-methoxyphenyl]acetamide APCI-MS: m/z 462 [MH+]

Example 41

N-[2-(3-{[1-(4-Chlorobenzyl)-4-piperidinyl]amino}-2-hydroxypropoxy)-6-fluorophenyl]acetamide APCI-MS: m/z 450 [MH+]

Example 42

N-[2-Fluoro-6-(3-{[1-fluorobenzyl)-4-piperidinyl]amino}-2-hydroxypropoxy)phenyl]acetamide APCI-MS: m/z 434 [MH+]

Example 43

2-(3-{[1-(4-Chlorobenzyl)-4-piperidinyl]amino}-2-hydroxy-2-methylpropoxy)N-methylbenzamide APCI-MS: m/z 446 [MH+]

Example 44

N-(2-{3-[1-(3,4-Dichloro-benzyl)-piperidin-4-ylamino]-2-hydroxy-propoxy}-phenyl)-benzamide To a solution of N-(2-Oxiranylmethoxy-phenyl)-benzamide (0.2 ml, 0.1M in DMSO) was added (0.2 ml, 0.1M in EtOH) of 1-(3,4-Dichloro-benzyl)-piperidin-4-ylamine. The resulting mixture was heated at 75-80° C. for 24 hours. The ethanol was removed and the product was purified with preparative LC/MS.

APCI-MS: m/z 529[MH$^+$]

The following Examples 45-63 were synthesised by methods analogous to the method described in Example 44.

Example 45

N-(2-{3-[1-(3-Chloro-4-fluoro-benzyl)-piperidin-4-ylamino]-2-hydroxy-propoxy}-phenyl)-benzamide APCI-MS: m/z 513[MH$^+$]

Example 46

N-(2-{3-[1-(3,4-Difluoro-benzyl)-piperidin-4-ylamino]-2-hydroxy-propoxy}-phenyl)-benzamide APCI-MS: m/z 496[MH$^+$]

Example 47

N-(2-{3-[1-(3,4-Dichloro-benzyl)-piperidin-4-ylamino]-2-hydroxy-propoxy}-6-methyl-phenyl)-acetamide APCI-MS: m/z 481[MH$^+$]

Example 48

N-(2-{3-[1-(4-Fluoro-benzyl)-piperidin-4-ylamino]-2-hydroxy-propoxy}-6-methyl-phenyl)-acetamide APCI-MS: m/z 430[MH$^+$]

Example 49

N-(2-{3-[1-(4-Bromo-benzyl)-piperidin-4-ylamino]-2-hydroxy-2-methyl-propoxy}-phenyl)-acetamide APCI-MS: m/z 490[M+]

Example 50

N(2-{3-[1-(3,4-Dichloro-benzyl)-piperidin-4-ylamino]-2-hydroxy-2-methyl-propoxy}phenyl)-acetamide APCI-MS: m/z 481[MH$^+$]

Example 51

N-(2-{3-[1-(3-Chloro-4-fluoro-benzyl)-piperidin-4-ylamino]-2-hydroxy-2-methyl-propoxy}-phenyl)-acetamide APCI-MS: m/z 464[MH$^+$]

Example 52

N-(2-{3-[1-(3,4-Difluoro-benzyl)-piperidin-4-ylamino]-2-hydroxy-2-methyl-propoxy}-phenyl)-acetamide APCI-MS: m/z 448[MH$^+$]

Example 53

2-{3-[1-(4-Bromo-benzyl)-piperidin-4-ylamino]-2-hydroxy-propoxy}-N-methyl-benzamide APCI-MS: m/z 476[M$^+$]

Example 54

2-{3-[1-(3,4-Dichloro-benzyl)-piperidin-4-ylamino]-2-hydroxy-propoxy}-N-methyl-benzamide APCI-MS: m/z 467[M$^+$]

Example 55

2-{3-[1-(4-Chloro-benzyl)-piperidin-4-ylamino]-2-hydroxy-propoxy}-N-methyl-benzamide APCI-MS: m/z 432[MH$^+$]

Example 56

2-{3-[1-(4-Fluoro-benzyl)-piperidin-4-ylamino]-2-hydroxy-propoxy}-N-methyl-benzamide APCI-MS: m/z 416[MH$^+$]

Example 57

3,5-Dimethyl-1H-pyrrole-2-carboxylic Acid (2-{3-[1-(4-bromo-benzyl)-piperidin-4-ylamino]-2-hydroxy-propoxy}-phenyl)-amide APCI-MS: m/z 456[MH$^+$]

Example 58

3,5-Dimethyl-1H-pyrrole-2-carboxylic Acid (2-{3-[1-(3-chloro-benzyl)-piperidin-4-ylamino]-2-hydroxy-propoxy}-phenyl)-amide APCI-MS: m/z 512[MH$^+$]

Example 59

3,5-Dimethyl-1H-pyrrole-2-carboxylic Acid (2-{3-[1-(3-fluoro-benzyl)-piperidin-4-ylamino]-2-hydroxy-propoxy}-phenyl)amide APCI-MS: m/z 495[MH$^+$]

Example 60

N-(2-{3-[1-(4-Bromo-benzyl)-piperidin-4-ylamino]-2-hydroxy-propoxy}-phenyl)-acetamide APCI-MS: m/z 476[M$^+$]

Example 61

N-(2-{3-[1-(3-Chloro-4-fluoro-benzyl)-piperidin-4-ylamino]-2-hydroxy-propoxy}-phenyl)acetamide APCI-MS: m/z 450[MH$^+$]

Example 62

N-(2-{3-[1-(3,4-Difluoro-benzyl)-piperidin-4-ylamino]-2-hydroxy-propoxy}-phenyl)-acetamide APCI-MS: m/z 434[MH$^+$]

Example 63

N-(2-{3-[1-(4-Fluoro-benzyl)-piperidin-4-ylamino]-2-hydroxy-propoxy}-phenyl)-acetamide APCI-MS: m/z 416[MH$^+$]

THP-1 Chemotaxis Assay

Introduction

The assay measured the chemotactic response elicited by MIP-1α chemokine in the human monocytic cell line THP-1. The compounds of the Examples were evaluated by their ability to depress the chemotactic response to a standard concentration of MIP-1α chemokine.

Methods

Culture of THP-1 Cells

Cells were thawed rapidly at 37° C. from frozen aliquots and resuspended in a 25 cm flask containing 5 ml of RPMI-1640 medium supplemented with Glutamax and 10% heat inactivated fetal calf serum without antibiotics (RPMI+10% HIFCS). At day 3 the medium is discarded and replaced with fresh medium.

THP-1 cells are routinely cultured in RPMI-1640 medium supplemented with 10% heat inactivated fetal calf serum and glutamax but without antibiotics. Optimal growth of the cells requires that they are passaged every 3 days and that the minimum subculture density is 4×10+5 cells/ml.

Chemotaxis Assay

Cells were removed from the flask and washed by centrifugation in RPMI+10% HIFCS+glutamax. The cells were then resuspended at 2×10+7 cells/ml in fresh medium (RPMI+10% HIFCS+glutamax) to which was added calcein-AM (5 μl of stock solution to 1 ml to give a final concentration of 5×10$^{-6}$M). After gentle mixing the cells were incubated at 37° C. in a CO$_2$ incubator for 30 minutes. The cells were then diluted to 50 ml with medium and washed twice by centrifugation at 400×g. Labelled cells were then resuspended at a cell concentration of 1×10+7 cells/ml and incubated with an equal volume of MIP-1α antagonist (10$^{-10}$M to 10$^{-6}$M final concentration) for 30 minutes at 37° C. in a humidified CO$_2$ incubator.

Chemotaxis was performed using Neuroprobe 96-well chemotaxis plates employing 8 μm filters (cat no. 101-8). Thirty microlitres of chemoattractant supplemented with various concentrations of antagonists or vehicle were added to the lower wells of the plate in triplicate. The filter was then carefully positioned on top and then 25 μl of cells preincubated with the corresponding concentration of antagonist or vehicle were added to the surface of the filter. The plate was then incubated for 2 hours at 37° C. in a humidified CO$_2$ incubator. The cells remaining on the surface were then removed by adsorption and the whole plate was centrifuged at 2000 rpm for 10 minutes. The filter was then removed and the cells that had migrated to the lower wells were quantified by the fluorescence of cell associated calcein-AM. Cell migration was then expressed in fluorescence units after subtraction of the reagent blank and values were standardized to % migration by comparing the fluorescence values with that of a known number of labelled cells. The effect of antagonists was calculated as % inhibition when the number of migrated cells were compared with vehicle.

The invention claimed is:

1. A compound of general formula

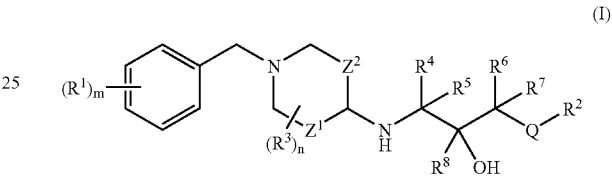

(I)

wherein m is 0, 1, 2 or 3;

each $R^1$ independently represents halogen, cyano, nitro, carboxyl, hydroxyl, $C_3$-$C_6$ cycloalkyl, $C_1$-$C_6$ alkoxy, $C_1$-$C_6$ alkoxycarbonyl, $C_1$-$C_6$ haloalkyl, $C_1$-$C_6$ haloalkoxy, —NR$^9$R$^{10}$, $C_3$-$C_6$ cycloalkylamino, $C_1$-$C_6$ alkylthio, $C_1$-$C_6$ alkylcarbonyl, $C_1$-$C_6$ alkylcarbonylamino, sulphonamido, $C_1$-$C_6$ alkylsulphonyl, —C(O)NR$^{11}$R$^{12}$, —NR$^{13}$C(O)—(NH)$_p$R$^{14}$, phenyl, or $C_1$-$C_6$ alkyl optionally substituted by carboxyl or $C_1$-$C_6$ alkoxycarbonyl;

p is 0 or 1;

$Z^1$ represents (CH$_2$)$_q$ where q is 1;

$Z^2$ represents CH$_2$;

Q represents an oxygen or sulphur atom or a group CH$_2$ or NH;

$R^2$ represents a group

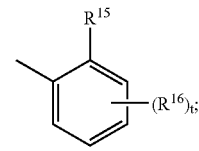

n is 0, 1 or 2;

each $R^3$ independently represents a $C_1$-$C_6$ alkyl, $C_1$-$C_6$ alkoxycarbonyl, —CH$_2$OH or carboxyl group;

$R^4$, $R^5$, $R^6$ and $R^6$ each independently represent a hydrogen atom or a $C_1$-$C_6$ alkyl group, or $R^4$, $R^5$, $R^6$ and $R^7$ together represent a $C_1$-$C_4$ alkylene chain linking the two carbon atoms to which they are attached to form a 4- to 7-membered saturated carbocycle, or $R^5$, $R^6$ and $R^7$ each represent a hydrogen atom and $R^4$ and $R^8$ together with the carbon atoms to which they are attached form a 5- to 6-membered saturated carbocycle;

$R^8$ represents a hydrogen atom, a $C_1$-$C_6$ alkyl group or is linked to $R^4$ as defined above;

$R^9$ and $R^{10}$ each independently represent a hydrogen atom or a $C_1$-$C_6$ alkyl group, or $R^9$ and $R^{10}$ together with the nitrogen atom to which they are attached form a 4- to 7-membered saturated heterocycle;

$R^{11}$ and $R^{12}$ each independently represent a hydrogen atom or a $C_1$-$C_6$ alkyl group optionally substituted by $C_1$-$C_6$ alkoxycarbonyl;

$R^{13}$ represents a hydrogen atom or a $C_1$-$C_6$ alkyl group;

$R^{14}$ represents a hydrogen atom, or a $C_1$-$C_6$ alkyl group optionally substituted by carboxyl, $C_1$-$C_6$ alkoxy or $C_1$-$C_6$ alkoxycarbonyl;

$R^{15}$ represents carboxyl, $C_1$-$C_6$ alkoxy, $C_1$-$C_6$ alkylcarbonyl, $C_1$-$C_6$ alkoxycarbonyl, $C_1$-$C_6$ alkoxycarbonyl$C_1$-$C_6$ alkyl or a group —$NR^{17}R^{18}$, —$NHSO_2CH_3$, —$C(O)NR^{17}R^{18}$, —$NHC(O)NR^{17}R^{18}$, —$OC(O)NR^{17}R^{18}$, —$OCH_2C(O)NR^{17}R^{18}$, —$NHC(O)OR^{19}$ or —$NHC(O)R^{20}$;

t is 0, 1, 2 or 3;

each $R^{16}$ independently represents halogen, cyano, nitro, carboxyl, hydroxyl, $C_3$-$C_6$ cycloalkyl, $C_1$-$C_6$ alkoxy, $C_1$-$C_6$ alkoxycarbonyl, $C_1$-$C_6$ haloalkyl, $C_1$-$C_6$ haloalkoxy, —$NR^{21}R^{22}$, $C_3$-$C_6$ cycloalkylamino, $C_1$-$C_6$ alkylthio, $C_1$-$C_6$ alkylcarbonyl, $C_1$-$C_6$ alkylcarbonylamino, sulphonamido, $C_1$-$C_6$ alkylsulphonyl, —$C(O)NR^{23}R^{24}$, —$NR^{25}C(O)(NH)_vR^{26}$, phenyl, or $C_1$-$C_6$ alkyl optionally substituted by carboxyl or $C_1$-$C_6$ alkoxycarbonyl;

$R^{17}$ and $R^{18}$ each independently represent a hydrogen atom, or a $C_1$-$C_6$ alkyl group optionally substituted by carboxyl or $C_1$-$C_6$ alkoxycarbonyl, or $R^{17}$ and $R^{18}$ together with the nitrogen atom to which they are attached form a 4- to 7-membered saturated heterocycle;

$R^{19}$ represents a hydrogen atom, or a $C_1$-$C_6$ alkyl group optionally substituted by carboxyl or $C_1$-$C_6$ alkoxycarbonyl;

$R^{20}$ represents a group $C_1$-$C_6$ alkyl, $C_2$-$C_6$ alkenyl, $C_3$-$C_6$ cycloalkyl, adamantyl, $C_5$-$C_6$ cycloalkenyl, phenyl or a saturated or unsaturated 5- to 10-membered heterocyclic ring system comprising at least one heteroatom selected from nitrogen, oxygen and sulphur, each of which may be optionally substituted by one or more substituents independently selected from nitro, hydroxyl, oxo, halogen, carboxyl, $C_1$-$C_6$ alkyl, $C_1$-$C_6$ alkoxy, $C_1$-$C_6$ alkylthio, $C_1$-$C_6$ alkylcarbonyl, $C_1$-$C_6$ alkoxycarbonyl, phenyl and —$NHC(O)$—$R^{27}$;

$R^{21}$ and $R^{22}$ each independently represent a hydrogen atom or a $C_1$-$C_6$ alkyl group, or $R^{21}$ and $R^{22}$ together with the nitrogen atom to which they are attached form a 4- to 7-membered saturated heterocycle;

$R^{24}$ and $R^{23}$ each independently represent a hydrogen atom or a $C_1$-$C_6$ alkyl group optionally substituted by $C_1$-$C_6$ alkoxycarbonyl;

v is 0 or 1;

$R^{25}$ represents a hydrogen atom or a $C_1$-$C_6$ alkyl group;

$R^{26}$ represents a hydrogen atom, or a $C_1$-$C_6$ alkyl group optionally substituted by carboxyl, $C_1$-$C_6$ alkoxy or $C_1$-$C_6$ alkoxycarbonyl; and $R^{27}$ represents a $C_1$-$C_6$ alkyl, amino (—$NH_2$) or phenyl group;

or a pharmaceutically acceptable salt thereof.

2. A compound according to claim 1, wherein m is 1 or 2.

3. A compound according to claim 2, wherein each $R^1$ represents a halogen atom.

4. A compound according to claim 1, wherein Q represents an oxygen atom.

5. A compound according to claim 1, wherein $R^{15}$ represents a group —$NHC(O)R^{20}$.

6. A compound according to claim 3, wherein Q represents an oxygen atom.

7. A compound according to claim 3, wherein $R^{15}$ represents a group —$NHC(O)R^{20}$.

8. A compound according to claim 6, wherein $R^{15}$ represents a group —$NHC(O)R^{20}$.

9. A compound according to claim 8, wherein m is 1 and $R^1$ is chlorine.

10. A compound according to claim 9, wherein $R^{16}$ is hydroxyl.

11. A compound according to claim 10, wherein $R^{20}$ is methyl.

12. A compound according to claim 11, wherein $R^8$ is methyl.

13. A compound according to claim 12, wherein each of $R^4$, $R^5$, $R^6$ and $R^7$ is H.

14. A compound according to claim 13, wherein n is 0.

15. A compound according to claim 1, wherein each of $R^4$, $R^5$, $R^6$ and $R^7$ is H.

16. A compound according to claim 15, wherein $R^8$ is methyl.

17. A compound according to claim 1, wherein n is 0.

18. A process for the preparation of a compound of formula (I) as defined in claim 1 which comprises, (a) reacting a compound of general formula

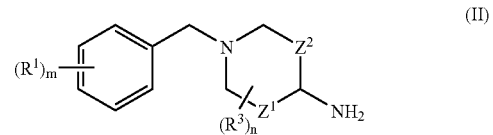

wherein m, n, $Z^1$, $Z^2$, $R^1$ and $R^3$ are as defined in formula (I), with a compound of general formula

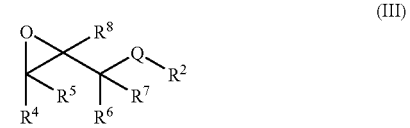

wherein Q, $R^2$, $R^4$, $R^5$, $R^6$, $R^7$ and $R^8$ are as defined in formula (I); or (b) reacting a compound of general formula

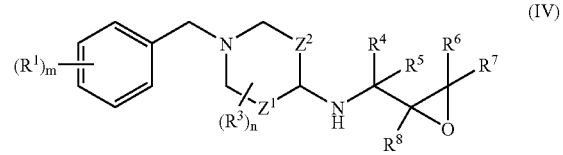

wherein m, n, $Z^1$, $Z^2$, $R^1$, $R^3$, $R^4$, $R^5$, $R^6$ and $R^8$ are as defined in formula (I), with a compound of general formula

wherein L represents a hydrogen atom or a leaving group and Q and $R^2$ are as defined in formula (I); or (c) reacting a compound of general formula

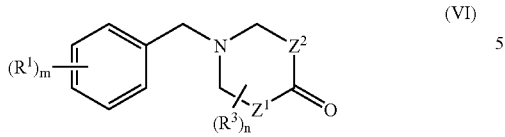
(VI)

wherein m, n, $Z^1$, $Z^2$, $R^1$ and $R^3$ are as defined in formula (I), with a compound of general formula

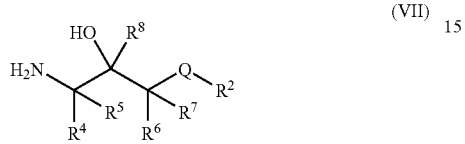
(VII)

wherein Q, $R^2$, $R^4$, $R^5$, $R^6$, $R^7$ and $R^8$ are as defined in formula (I);

and optionally after (a), (b) or (c) converting the compound of formula (I) to a further compound of formula (I) and/or forming a pharmaceutically acceptable salt of the compound of formula (I).

19. A pharmaceutical composition comprising a compound of formula (I), or a pharmaceutically acceptable salt thereof, as claimed in claim 1 in association with a pharmaceutically acceptable adjuvant, diluent or carrier.

20. A process for the preparation of a pharmaceutical composition which comprises mixing a compound of formula (I), or a pharmaceutically acceptable salt thereof, as claimed in claim 1 with a pharmaceutically acceptable adjuvant, diluent or carrier.

21. A method of treating an inflammatory disease in a patient suffering from, said disease, which comprises administering to the patient a therapeutically effective amount of a compound of formula (I):

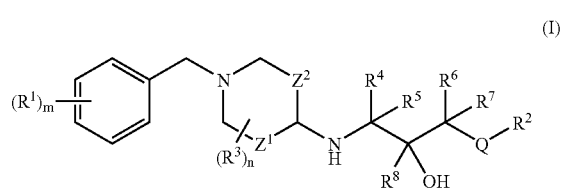
(I)

wherein m is 0, 1, 2 or 3;

each $R^1$ independently represents halogen, cyano, nitro, carboxyl, hydroxyl, $C_3$-$C_6$ cycloalkyl, $C_1$-$C_6$ alkoxy, $C_1$-$C_6$ alkoxycarbonyl, $C_1$-$C_6$ haloalkyl, $C_1$-$C_6$ haloalkoxy, —$NR^9R^{10}$, $C_3$-$C_6$ cycloalkylamino, $C_1$-$C_6$ alkylthio, $C_1$-$C_6$ alkylcarbonyl, $C_1$-$C_6$ alkylcarbonylamino, sulphonamido, $C_1$-$C_6$ alkylsulphonyl, —C(O)$NR^{11}R^{12}$, —$NR^{13}$C(O)—(NH)$_p R^{14}$, phenyl, or $C_1$-$C_6$ alkyl optionally substituted by carboxyl or $C_1$-$C_6$ alkoxycarbonyl;

p is 0 or 1;

$Z^1$ represents a bond or a group $(CH_2)_q$ where q is 1 or 2;

$Z^2$ represents a bond or a group $CH_2$, with the proviso that $Z^1$ and $Z^2$ do not both simultaneously represent a bond;

Q represents an oxygen or sulphur atom or a group $CH_2$ or NH;

$R^2$ represents a group

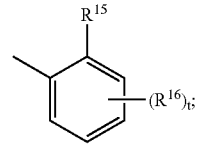

n is 0, 1 or 2;

each $R^3$ independently represents a $C_1$-$C_6$ alkyl, $C_1$-$C_6$ alkoxycarbonyl, —$CH_2OH$ or carboxyl group;

$R^4$, $R^5$, $R^6$ and $R^7$ each independently represent a hydrogen atom or a $C_1$-$C_6$ alkyl group, or $R^4$, $R^5$, $R^6$ and $R^7$ together represent a $C_1$-$C_4$ alkylene chain linking the two carbon atoms to which they are attached to form a 4- to 7-membered saturated carbocycle, or $R^5$, $R^6$ and $R^7$ each represent a hydrogen atom and $R^4$ and $R^8$ together with the carbon atoms to which they are attached form a 5- to 6-membered saturated carbocycle;

$R^8$ represents a hydrogen atom, a $C_1$-$C_6$ alkyl group or is linked to $R^4$ as defined above;

$R^9$ and $R^{10}$ each independently represent a hydrogen atom or a $C_1$-$C_6$ alkyl group, or $R^9$ and $R^{10}$ together with the nitrogen atom to which they are attached form a 4- to 7-membered saturated heterocycle;

$R^{11}$ and $R^{12}$ each independently represent a hydrogen atom or a $C_1$-$C_6$ alkyl group optionally substituted by $C_1$-$C_6$ alkoxycarbonyl;

$R^{13}$ represents a hydrogen atom or a $C_1$-$C_6$ alkyl group;

$R^{14}$ represents a hydrogen atom, or a $C_1$-$C_6$ alkyl group optionally substituted by carboxyl, $C_1$-$C_6$ alkoxy or $C_1$-$C_6$ alkoxycarbonyl;

$R^{15}$ represents carboxyl, $C_1$-$C_6$ alkoxy, $C_1$-$C_6$ alkylcarbonyl, $C_1$-$C_6$ alkoxycarbonyl, $C_1$-$C_6$ alkoxycarbonyl$C_1$-$C_6$ alkyl or a group —$NR^{17}R^{18}$, —$NHSO_2CH_3$, —C(O)$NR^{17}R^{18}$, —NHC(O)$NR^{17}R^{18}$, —OC(O)$NR^{17}R^{18}$, —$OCH_2$C(O)$NR^{17}R^{18}$, —NHC(O)$OR^{19}$ or —NHC(O)$R^{20}$;

t is 0, 1, 2 or 3;

each $R^{16}$ independently represents halogen, cyano, nitro, carboxyl, hydroxyl, $C_3$-$C_6$ cycloalkyl, $C_1$-$C_6$ alkoxy, $C_1$-$C_6$ alkoxycarbonyl, $C_1$-$C_6$ haloalkyl, $C_1$-$C_6$ haloalkoxy, —$NR^{21}R^{22}$, $C_3$-$C_6$ cycloalkylamino, $C_1$-$C_6$ alkylthio, $C_1$-$C_6$ alkylcarbonyl, $C_1$-$C_6$ alkylcarbonylamino, sulphonamido, $C_1$-$C_6$ alkylsulphonyl, —C(O)$NR^{23}R^{24}$, —$NR^{25}C(O)(NH)_v R^{26}$, phenyl, $C_2$-$C_6$ alkyl, or $C_1$-$C_6$ alkyl substituted by carboxyl or $C_1$-$C_6$ alkoxycarbonyl;

$R^{17}$ and $R^{18}$ each independently represent a hydrogen atom, or a $C_1$-$C_6$ alkyl group optionally substituted by carboxyl or $C_1$-$C_6$ alkoxycarbonyl, or $R^{17}$ and $R^{18}$ together with the nitrogen atom to which they are attached form a 4- to 7-membered saturated heterocycle;

$R^{19}$ represents a hydrogen atom, or a $C_1$-$C_6$ alkyl group optionally substituted by carboxyl or $C_1$-$C_6$ alkoxycarbonyl;

$R^{20}$ represents a group $C_1$-$C_6$ alkyl, $C_2$-$C_6$ alkenyl, $C_3$-$C_6$ cycloalkyl, adamantyl, $C_5$-$C_6$ cycloalkenyl, phenyl or a saturated or unsaturated 5- to 10-membered heterocyclic ring system comprising at least one heteroatom selected from nitrogen, oxygen and sulphur, each of which may be optionally substituted by one or more substituents independently selected from nitro, hydroxyl, oxo, halogen, carboxyl, $C_1$-$C_6$ alkyl, $C_1$-$C_6$ alkoxy, $C_1$-$C_6$ alkylthio, $C_1$-$C_6$ alkylcarbonyl, $C_1$-$C_6$ alkoxycarbonyl, phenyl and —NHC(O)—$R^{27}$;

$R^{21}$ and $R^{22}$ each independently represent a hydrogen atom or a $C_1$-$C_6$ alkyl group, or $R^{21}$ and $R^{22}$ together with the nitrogen atom to which they are attached form a 4- to 7-membered saturated heterocycle;

$R^{23}$ and $R^{24}$ each independently represent a hydrogen atom or a $C_1$-$C_6$ alkyl group optionally substituted by $C_1$-$C_6$ alkoxycarbonyl;

v is 0 or 1;

$R^{25}$ represents a hydrogen atom or a $C_1$-$C_6$ alkyl group;

$R^{26}$ represents a hydrogen atom, or a $C_1$-$C_6$ alkyl group optionally substituted by carboxyl, $C_1$-$C_6$ alkoxy or $C_1$-$C_6$ alkoxycarbonyl; and $R^{27}$ represents a $C_1$-$C_6$ alkyl, amino (—$NH_2$) or phenyl group;

or a pharmaceutically acceptable salt thereof.

22. A method of treating chronic obstructive pulmonary disease in a patient suffering from, said disease, which comprises administering to the patient a therapeutically effective amount of a compound of formula (I):

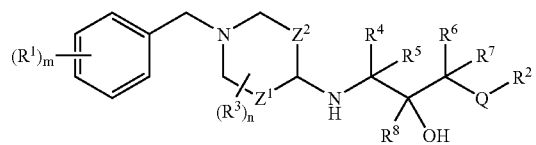

(I)

wherein
m is 0, 1, 2 or 3;

each $R^1$ independently represents halogen, cyano, nitro, carboxyl, hydroxyl, $C_3$-$C_6$ cycloalkyl, $C_1$-$C_6$ alkoxy, $C_1$-$C_6$ alkoxycarbonyl, $C_1$-$C_6$ haloalkyl, $C_1$-$C_6$ haloalkoxy, —$NR^9R^{10}$, $C_3$-$C_6$ cycloalkylamino, $C_1$-$C_6$ alkylthio, $C_1$-$C_6$ alkylcarbonyl, $C_1$-$C_6$ alkylcarbonylamino, suiphonamido, $C_1$-$C_6$ alkylsulphonyl, —C(O)$NR^{11}R^{12}$, —$NR^{13}$C(O)—$(NH)_pR^{14}$, phenyl, or $C_1$-$C_6$ alkyl optionally substituted by carboxyl or $C_1$-$C_6$ alkoxycarbonyl;

p is 0 or 1;

$Z^1$ represents a bond or a group $(CH_2)_q$ where q is 1 or 2;

$Z^2$ represents a bond or a group $CH_2$, with the proviso that $Z^1$ and $Z^2$ do not both simultaneously represent a bond;

Q represents an oxygen or sulphur atom or a group $CH_2$ or NH;

$R^2$ represents a group

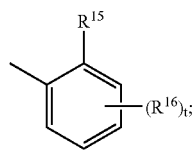

n is 0, 1 or 2;

each $R^3$ independently represents a $C_1$-$C_6$ alkyl, $C_1$-$C_6$ alkoxycarbonyl, —$CH_2OH$ or carboxyl group;

$R^4$, $R^5$, $R^6$ and $R^7$ each independently represent a hydrogen atom or a $C_1$-$C_6$ alkyl group, or $R^4$, $R^5$, $R^6$ and $R^7$ together represent a $C_1$-$C_4$ alkylene chain linking the two carbon atoms to which they are aftached to form a 4- to 7-membered saturated carbocycle, or $R^5$, $R^6$ and $R^7$ each represent a hydrogen atom and $R^4$ and $R^8$ together with the carbon atoms to which they are attached form a 5- to 6-membered saturated carbocycle;

$R^8$ represents a hydrogen atom, a $C_1$-$C_6$ alkyl group or is linked to $R^4$ as defined above;

$R^9$ and $R^{10}$ each independently represent a hydrogen atom or a $C_1$-$C_6$ alkyl group, or $R^9$ and $R^{10}$ together with the nitrogen atom to which they are attached form a 4- to 7-membered saturated heterocycle;

$R^{11}$ and $R^{12}$ each independently represent a hydrogen atom or a $C_1$-$C_6$ alkyl group optionally substituted by $C_1$-$C_6$ alkoxycarbonyl;

$R^{13}$ represents a hydrogen atom or a $C_1$-$C_6$ alkyl group;

$R^{14}$ represents a hydrogen atom, or a $C_1$-$C_6$ alkyl group optionally substituted by carboxyl, $C_1$-$C_6$ alkoxy or $C_1$-$C_6$ alkoxycarbonyl;

$R^{15}$ represents carboxyl, $C_1$-$C_6$ alkoxy, $C_1$-$C_6$ alkylcarbonyl, $C_1$-$C_6$ alkoxycarbonyl, $C_1$-$C_6$ alkoxycarbonyl$C_1$-$C_6$ alkyl or a group —$NR^{17}R^{18}$, —$NHSO_2CH_3$, —C(O)$NR^{17}R^{18}$, —NHC(O)$NR^{17}R^{18}$, —OC(O)$NR^{17}R^{18}$, —$OCH_2$C(O)$NR^{17}R^{18}$, —NHC(O)$OR^{19}$ or —NHC(O)$R^{20}$;

t is 0, 1, 2 or 3;

each $R^{16}$ independently represents halogen, cyano, nitro, carboxyl, hydroxyl, $C_3$-$C_6$ cycloalkyl, $C_1$-$C_6$ alkoxy, $C_1$-$C_6$ alkoxycarbonyl, $C_1$-$C_6$ haloalkyl, $C_1$-$C_6$ haloalkoxy, —$NR^{21}R^{22}$, $C_3$-$C_6$ cycloalkylamino, $C_1$-$C_6$ alkylthio, $C_1$-$C_6$ alkylcarbonyl, $C_1$-$C_6$ alkylcarbonylamino, sulphonamido, $C_1$-$C_6$ alkylsulphonyl, —C(O)$NR^{23}R^{24}$, —$NR^{25}$C(O)$(NH)_vR^{26}$, phenyl, $C_2$-$C_6$ alkyl, or $C_1$-$C_6$ alkyl substituted by carboxyl or $C_1$-$C_6$ alkoxycarbonyl;

$R^{17}$ and $R^{18}$ each independently represent a hydrogen atom, or a $C_1$-$C_6$ alkyl group optionally substituted by carboxyl or $C_1$-$C_6$ alkoxycarbonyl, or $R^{17}$ and $R^{17}$ together with the nitrogen atom to which they are attached form a 4- to 7-membered saturated heterocycle;

$R^{19}$ represents a hydrogen atom, or a $C_1$-$C_6$ alkyl group optionally substituted by carboxyl or $C_1$-$C_6$ alkoxycarbonyl;

$R^{20}$ represents a group $C_1$-$C_6$ alkyl, $C_2$-$C_6$ alkenyl, $C_3$-$C_6$ cycloalkyl, adamantyl, $C_5$-$C_6$ cycloalkenyl, phenyl or a saturated or unsaturated 5- to 10-membered heterocyclic ring system comprising at least one heteroatom selected from nitrogen, oxygen and sulphur, each of which may be optionally substituted by one or more substituents independently selected from nitro, hydroxyl, oxo, halogen, carboxyl, $C_1$-$C_6$ alkyl, $C_1$-$C_6$ alkoxy, $C_1$-$C_6$ alkylthio, $C_1$-$C_6$ alkylcarbonyl, $C_1$-$C_6$ alkoxycarbonyl, phenyl and —NHC(O)—$R^{27}$;

$R^{21}$ and $R^{22}$ each independently represent a hydrogen atom or a $C_1$-$C_6$ alkyl group, or $R^{21}$ and $R^{22}$ together with the nitrogen atom to which they are attached form a 4- to 7-membered saturated heterocycle;

$R^{23}$ and $R^{24}$ each independently represent a hydrogen atom or a $C_1$-$C_6$ alkyl group optionally substituted by $C_1$-$C_6$ alkoxycarbonyl;

v is 0 or 1;

$R^{25}$ represents a hydrogen atom or a $C_1$-$C_6$ alkyl group;

$R^{26}$ represents a hydrogen atom, or a $C_1$-$C_6$ alkyl group optionally substituted by carboxyl, $C_1$-$C_6$ alkoxy or $C_1$-$C_6$ alkoxycarbonyl; and $R^{27}$ represents a $C_1$-$C_6$ alkyl, amino (—$NH_2$) or phenyl group;

or a pharmaceutically acceptable salt thereof.

23. A method of treating asthma in a patient suffering from, said disease, which comprises administering to the patient a therapeutically effective amount of a compound of formula (I):

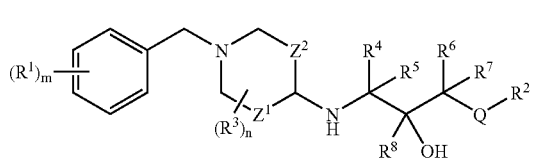

wherein
m is 0, 1, 2 or 3;
each $R^1$ independently represents halogen, cyano, nitro, carboxyl, hydroxyl, $C_3$-$C_6$ cycloalkyl, $C_1$-$C_6$ alkoxy, $C_1$-$C_6$ alkoxycarbonyl, $C_1$-$C_6$ haloalkyl, $C_1$-$C_6$ haloalkoxy, —$NR^9R^{10}$, $C_3$-$C_6$ cycloalkylamino, $C_1$-$C_6$ alkylthio, $C_1$-$C_6$ alkylcarbonyl, $C_1$-$C_6$ alkylcarbonylamino, sulphonamido, $C_1$-$C_6$ alkylsulphonyl, —C(O)$NR^{11}R^{12}$, —$NR^{13}$C(O)—$(NH)_pR^{14}$, phenyl, or $C_1$-$C_6$ alkyl optionally substituted by carboxyl or $C_1$-$C_6$ alkoxycarbonyl;
p is 0 or 1;
$Z^1$ represents a bond or a group $(CH_2)_q$ where q is 1 or 2;
$Z^2$ represents a bond or a group $CH_2$, with the proviso that $Z^1$ and $Z^2$ do not both simultaneously represent a bond;
Q represents an oxygen or sulphur atom or a group $CH_2$ or NH;
$R^2$ represents a group

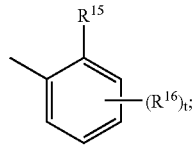

n is 0, 1 or 2;
each $R^3$ independently represents a $C_1$-$C_6$ alkyl, $C_1$-$C_6$ alkoxycarbonyl, —$CH_2OH$ or carboxyl group;
$R^4$, $R^5$, $R^6$ and $R^7$ each independently represent a hydrogen atom or a $C_1$-$C_6$ alkyl group, or $R^4$, $R^5$, $R^6$ and $R^7$ together represent a $C_1$-$C_4$ alkylene chain linking the two carbon atoms to which they are attached to form a 4- to 7-membered saturated carbocycle, or $R^5$, $R^6$ and $R^7$ each represent a hydrogen atom and $R^4$ and $R^8$ together with the carbon atoms to which they are attached form a 5- to 6-membered saturated carbocycle;
$R^8$ represents a hydrogen atom, a $C_1$-$C_6$ alkyl group or is linked to as defined above;
$R^9$ and $R^{10}$ each independently represent a hydrogen atom or a $C_1$-$C_6$ alkyl group, or $R^9$ and $R^{10}$ together with the nitrogen atom to which they are attached form a 4- to 7-membered saturated heterocycle;
$R^{11}$ and $R^{12}$ each independently represent a hydrogen atom or a $C_1$-$C_6$ alkyl group optionally substituted by $C_1$-$C_6$ alkoxycarbonyl;
$R^{13}$ represents a hydrogen atom or a $C_1$-$C_6$ alkyl group;
$R^{14}$ represents a hydrogen atom, or a $C_1$-$C_6$ alkyl group optionally substituted by carboxyl, $C_1$-$C_6$ alkoxy or $C_1$-$C_6$ alkoxycarbonyl;
$R^{15}$ represents carboxyl, $C_1$-$C_6$ alkoxy, $C_1$-$C_6$ alkylcarbonyl, $C_1$-$C_6$ alkoxycarbonyl, $C_1$-$C_6$ alkoxycarbonyl$C_1$-$C_6$ alkyl or a group —$NR^{17}R^{18}$, —$NHSO_2CH_3$, —C(O)$NR^{17}R^{18}$, —NHC(O)$NR^{17}R^{18}$, —OC(O)$NR^{17}R^{18}$, —$OCH_2C(O)NR^{17}R^{18}$, —NHC(O)$OR^{19}$ or —NHC(O)$R^{20}$;
t is 0, 1, 2 or 3;
each $R^{16}$ independently represents halogen, cyano, nitro, carboxyl, hydroxyl, $C_3$-$C_6$ cycloalkyl, $C_1$-$C_6$ alkoxy, $C_1$-$C_6$ alkoxycarbonyl, $C_1$-$C_6$ haloalkyl, $C_1$-$C_6$ haloalkoxy, —$NR^{21}R^{22}$, $C_3$-$C_6$ cycloalkylamino, $C_1$-$C_6$ alkylthio, $C_1$-$C_6$ alkylcarbonyl, $C_1$-$C_6$ alkylcarbonylamino, sulphonamido, $C_1$-$C_6$ alkylsulphonyl, —C(O)$NR^{23}R^{24}$, —$NR^{25}C(O)(NH)_vR^{26}$, phenyl, $C_2$-$C_6$ alkyl, or $C_1$-$C_6$ alkyl substituted by carboxyl or $C_1$-$C_6$ alkoxycarbonyl;
$R^{17}$ and $R^{18}$ each independently represent a hydrogen atom, or a $C_1$-$C_6$ alkyl group optionally substituted by carboxyl or $C_1$-$C_6$ alkoxycarbonyl, or $R^{17}$ and $R^{18}$ together with the nitrogen atom to which they are attached form a 4- to 7-membered saturated heterocycle;
$R^{19}$ represents a hydrogen atom, or a $C_1$-$C_6$ alkyl group optionally substituted by carboxyl or $C_1$-$C_6$ alkoxycarbonyl;
$R^{20}$ represents a group $C_1$-$C_6$ alkyl, $C_2$-$C_6$ alkenyl, $C_3$-$C_6$ cycloalkyl, adamantyl, $C_5$-$C_6$ cycloalkenyl, phenyl or a saturated or unsaturated 5- to 10-membered heterocyclic ring system comprising at least one heteroatom selected from nitrogen, oxygen and sulphur, each of which may be optionally substituted by one or more substituents independently selected from nitro, hydroxyl, oxo, halogen, carboxyl, $C_1$-$C_6$ alkyl, $C_1$-$C_6$ alkoxy, $C_1$-$C_6$ alkylthio, $C_1$-$C_6$ alkylcarbonyl, $C_1$-$C_6$ alkoxycarbonyl, phenyl and —NHC(O)—$R^{27}$;
$R^{21}$ and $R^{22}$ each independently represent a hydrogen atom or a $C_1$-$C_6$ alkyl group, or
$R^{21}$ and $R^{22}$ together with the nitrogen atom to which they are attached form a 4- to 7-membered saturated heterocycle;
$R^{23}$ and $R^{24}$ each independently represent a hydrogen atom or a $C_1$-$C_6$ alkyl group optionally substituted by $C_1$-$C_6$ alkoxycarbonyl;
v is 0 or 1;
$R^{25}$ represents a hydrogen atom or a $C_1$-$C_6$ alkyl group;
$R^{26}$ represents a hydrogen atom, or a $C_1$-$C_6$ alkyl group optionally substituted by carboxyl, $C_1$-$C_6$ alkoxy or $C_1$-$C_6$ alkoxycarbonyl; and
$R^{27}$ represents a $C_1$-$C_6$ alkyl, amino (—$NH_2$) or phenyl group;
or a pharmaceutically acceptable salt thereof.

* * * * *

UNITED STATES PATENT AND TRADEMARK OFFICE
CERTIFICATE OF CORRECTION

PATENT NO. : 7,528,156 B2
APPLICATION NO. : 10/994683
DATED : May 5, 2009
INVENTOR(S) : Tomas Eriksson, Tomas Klingstedt and Tesfaledet Mussie It is certified that error appears in the above-identified patent and that said Letters Patent is hereby corrected as shown below:

Title Page; item (57); Face of Patent, line 1 of Abstract, "(D" should read -- (I) --.

Column 28, line 60, "$R^6$ and $R^6$" should read -- $R^6$ and $R^7$ --.

Column 29, lines 27-28, "phenyl, or $C_1$-$C_6$ alkyl optionally substituted" should read -- phenyl, $C_2$-$C_6$ alkyl or $C_1$-$C_6$ alky substituted --.

Column 29, line 52, "$R^{24}$ and $R^{23}$" should read -- $R^{23}$ and $R^{24}$ --.

Column 30, line 61, "$R^6$ and $R^8$" should read -- $R^7$ and $R^8$ --.

Column 30, line 66, "L" should read -- $L^1$ --.

Column 31, line 36 (approximately), "inflammatory" should instead read -- airways --.

Column 33, line 40, "suiphonamido," should read -- sulphonamido, --.

Column 33, line 66, "aftached" should read -- attached --.

Column 34, line 36, "$R^{17}$ and $R^{17}$" should read -- $R^{17}$ and $R^{18}$ --.

Column 35, line 54, "to as" should read -- to $R^4$ as --.

Signed and Sealed this

Fifth Day of October, 2010

David J. Kappos
*Director of the United States Patent and Trademark Office*